United States Patent
Loken et al.

(10) Patent No.: US 9,880,155 B2
(45) Date of Patent: Jan. 30, 2018

(54) SYSTEM, METHOD, AND ARTICLE FOR DETECTING ABNORMAL CELLS USING MULTI-DIMENSIONAL ANALYSIS

(71) Applicant: Hematologics, Inc., Seattle, WA (US)

(72) Inventors: Michael R. Loken, Mercer Island, WA (US); Sanjaya N. Joshi, Kirkland, WA (US)

(73) Assignee: Hematologics, Inc., Seattle, WA (US)

( * ) Notice: Subject to any disclaimer, the term of this patent is extended or adjusted under 35 U.S.C. 154(b) by 426 days.

(21) Appl. No.: 14/098,278

(22) Filed: Dec. 5, 2013

(65) Prior Publication Data

US 2014/0221247 A1    Aug. 7, 2014

Related U.S. Application Data

(63) Continuation of application No. 11/357,359, filed on Feb. 17, 2006, now Pat. No. 8,630,833.

(60) Provisional application No. 60/654,265, filed on Feb. 18, 2005.

(51) Int. Cl.
| | |
|---|---|
| *G01N 33/48* | (2006.01) |
| *G01N 33/50* | (2006.01) |
| *G01N 15/14* | (2006.01) |
| *G01N 33/569* | (2006.01) |
| *G01N 33/574* | (2006.01) |
| *G06F 19/24* | (2011.01) |
| *G06K 9/00* | (2006.01) |
| *G06K 9/62* | (2006.01) |
| G06G 7/58 | (2006.01) |
| G01N 15/00 | (2006.01) |
| G06F 19/20 | (2011.01) |
| G06F 19/26 | (2011.01) |

(52) U.S. Cl.
CPC ..... *G01N 33/5091* (2013.01); *G01N 15/1456* (2013.01); *G01N 33/56966* (2013.01); *G01N 33/56972* (2013.01); *G01N 33/574* (2013.01); *G01N 33/57492* (2013.01); *G06F 19/24* (2013.01); *G06K 9/00147* (2013.01); *G06K 9/6218* (2013.01); *G06K 9/6254* (2013.01); *G01N 2015/0065* (2013.01); *G06F 19/20* (2013.01); *G06F 19/26* (2013.01)

(58) Field of Classification Search
CPC .................................................. G01N 33/582
See application file for complete search history.

(56) References Cited

U.S. PATENT DOCUMENTS

| | | |
|---|---|---|
| 5,795,727 A | 8/1998 | Bierre et al. |
| 2007/0112585 A1 | 5/2007 | Breiter et al. |

FOREIGN PATENT DOCUMENTS

EP    0 559 208    9/1993

OTHER PUBLICATIONS

International Search Report for PCT/US2006/005778, dated Nov. 2, 2006.
Civin et al., "Cell Surface Antigens on Human Marrow Cells: Dissection of Hematopoietic Development Using Monoclonal Antibodies and Multiparameter Flow Cytometry," *Concise Review International Journal of Cell Cloning*, 5:267-288, 1987.
Civin et al., "Cell Surface Antigens on Human Marrow Cells: Dissection of Hematopoietic Development Using Monoclonal Antibodies and Multiparameter Flow Cytometry," *Concise Reviews in Clinical and Experimental Hematology*, edited by Martin J. Murphy, Jr., pp. 149-159, 1992.
Coustan-Smith et al., "Clinical Importance of Minimal Residual Disease in Childhood Acute Lymphoblastic Leukemia," *Blood* 96:2691-2696, Oct. 15, 2000.
Dash et al., "'1+1>2': Merging Distance and Density Based Clustering," *Proceedings of the IEEE 7th International Conference on Database Systems for Advanced Applications (DASFAA '01)*, Hong Kong, China, Apr. 18-21, 2001, pp. 32-39.
Daszykowski et al., "Looking for natural patterns in data Part 1. Density-based approach," *Chemometrics and Intelligent Laboratory Systems* 56:83-92, 2001.
Ester et al., A Density-Based Algorithm for Discovering Clusters in Large Spatial Databases with Noise, *Proceedings of 2nd International Conference on Knowledge Discovery and Data Mining*, 1996.
Forgy, E., "Cluster Analysis of Multivariate Data: Efficiency vs. Interpretability of Classifications," *Biometrics*, 21:768-769, 1965.
Herzenberg et al., "Monoclonal Antibodies and the FACS: Complementary Tools for Immunobiology and Medicine," *Immunology Today* 21(8):383-90, Aug. 2000.
Hulett et al., "Cell Sorting: Automated Separation of Mammalian Cells as a Function of Intracellular Fluorescence," *Science* 166(3906):747-749, Nov. 1969.
Hulett et al., "Development and Application of a Rapid Cell Sorter," *Clin. Chem.* 19(8):813-816, 1973.
Hurwitz et al., Asynchronous Antigen Expression in B Lineage Acute Lymphoblastic Leukemia, *Blood* 72:299-307, Jul. 1998.
Judd et al., "Large-Scale Parallel Data Clustering," *IEEE Transactions on Pattern Analysis and Machine Intelligence* 20(8):871-876, Aug. 1998.
Kachel et al., "Eight-Parameter PC-AT Based Flow Cytometric Data System," *Cytometry* 11:805-812, 1990.
LeBein et al., "Multiparameter Flow Cytometric Analysis of Human Fetal Bone Marrow B Cells," *Leukemia* 4:354-358, May 1990.
Lin et al., "A Principal Component Clustering Approach to Object-Oriented Motion Segmentation and Estimation," *Journal of VLSI Signal Processing* 17:163-187, 1997.
Loken et al., "Analysis of Cell Populations with a Fluorescence-Activated Cell Sorter," *Ann. N.Y. Acad. of Sci.* 254:163-171, 1975.
Loken et al., "Cell Discrimination by Multiangle Light Scattering," *The Journal of Histochemistry and Cytochemistry* 24(1):284-291, 1976.

(Continued)

*Primary Examiner* — Eric S DeJong
(74) *Attorney, Agent, or Firm* — Seed IP Law Group LLP

(57) ABSTRACT

A system, method, and article for diagnosing a test set of biological cells. For example, in one embodiment a normal set of cells is characterized using flow cytometry. A centroid and radius are defined for a set of clusters in an n-dimensional space corresponding to a normal maturation for a cell lineage in the normal set of cells. A test set of cells is characterized using flow cytometry and the characterization is compared to the set of clusters.

8 Claims, 23 Drawing Sheets

(56) References Cited

OTHER PUBLICATIONS

Loken et al., "Characterization of Erythroid, Lymphoid and Monomyeloid Lineages in Normal Human Bone Marrow," *Flow Cytometry in Hematology*, Laerum OD, and Bjerksnes R. (eds.), Academic Press, New York, 1992, pp. 31-42.

Loken et al., "Flow Cytometric Analysis of Human Bone Marrow. I. Normal Erythroid Development," *Blood* 69(1):255-263, Jan. 1987.

Loken et al., "Flow Cytometric Analysis of Human Bone Marrow: II. Normal B Lymphocyte Development," *Blood* 70(5):1316-1324, Nov. 1987.

Loken et al., "Normal Antigen Expression in Hematopoiesis: Basis for Interpreting Leukemia Phenotypes," *Immunophenotyping*, Carleton Stewart and Janel K.A. Nicholson (eds.), Wiley-Liss, Inc., New York, 2000, pp. 133-160.

Lucio et al., Flow Cytometric Analysis of Normal B Cell Differentiation: A Frame of Reference for the Detection of Minimal Residual Disease in Precursor-B-ALL, *Leukemia* 13:419-427, 1999.

National Institute of Health, "Protein Reviews from the Web—Index of Information Available from PROW," URL= http://mpr.nci.nih.gov/RPOW/, retrieved Feb. 6, 2008.

Nickolayev et al., "Real-Time Statistical Clustering for Event Trace Reduction," *The International Journal of Supercomputer Applications and High Performance Computing* 11(2):144-159, 1997.

Press et al. (eds.), Numerical Recipes in C: The Art of Scientific Computing, Cambridge University Press, Cambridge, NY, 1992, pp. 591-606.

Reading et al., "Expression of Unusual Immunophenotype Combinations in Acute Myelogenous Leukemia," *Blood* 81(11):3083-3090, Jun. 1993.

Robinson et al., "*Current Protocols in Cytometry*," John Wiley & Sons, NY, NY, Eds. 1997-current. Cover Page and Table of Contents only.

Roederer et al., "8 Color, 10-Parameter Flow Cytometry to Elucidate Complex Leukocyte Heterogeneity," *Cytometry* 29:328-339, 1997.

San Miguel et al., "Early Immunophenotypical Evaluation of Minimal Residual Disease in Acute Myeloid Leukemia Identifies Different Patient Risk Groups and may Contribute to Postinduction Treatment Stratification," *Blood* 98(6):1746-1751, Sep. 2001.

Sheikholeslami et al., "WaveCluster: A Multi-Resolution Clustering Approach for Very Large Spatial Databases," *Proceedings of the 24th VLDB Conference*, New York, USA, 1998, pp. 428-439.

Shulman et al., The Biologic Significance of Rare Peripheral Blasts after Hematopoietic Cell Transplantation is Predicted by Multidimensional Flow Cytometry, *Am. J. Clin. Path.* 112:513-523, 1999.

Sievers et al., "Immunophenotypic Evidence of Leukemia after Induction Therapy Predicts Relapse: Results from a Prospective Children's Cancer Group Study of 252 Patients with Acute Myeloid Leukemia,"*Blood* 101(9): 3398-3406, May 2003.

Slater, et al., "On Locating a Facility to Service Areas within a Network," *Operations Research* 29(3):523-531, 1981.

Stockinger, H., et al., *Current Protocols in Immunology*, John Wiley & Sons, Inc., 2003, "Appendix 4A—Monoclonal Antibodies to Human Cell Surface Antigens," A.4A.1-A.4A.49.

Stockinger, H., et al., *Current Protocols in Immunology*, John Wiley & Sons, Inc., 2003, "Appendix 4B—Monoclonal Antibodies to Mouse Cell-Surface Antigens," A.4B.1-A.4B.25.

Stockinger, H., et al., *Current Protocols in Immunology*, John Wiley & Sons, Inc., 2003, "Appendix 4C—Monoclonal Antibodies to Rat Leukocyte Surface Antigens, MHC Antigens, and Immunoglobulins,"A.4C.1-A.4C.12.

Tattersall et al., "Packed hyper-ellipsoid classifiers," *Electronics Letters* 30(5):427-428, 1994.

Terstappen et al., "Flow Cytometric Characterization of Acute Myeloid Leukemia, Part II. Phenotypic Heterogeneity at Diagnosis," *Leukemia* 6:70-80, 1992.

Terstappen et al., Myeloid Cell Differentiation in Normal Bone Marrow and Acute Myeloid Leukemia Assessed by Multi-Dimensional Flow Cytometry, *Analytical Cellular Pathology* 2:229-240, 1990.

Tyree et al., "The Use of Linked Line Segments for Cluster Representation and Data Reductions," *Pattern Recognition Letters* 20(1):21-29, 1999.

Verwer et al., "Automatic Lineage Assignment of Acute Leukemias by Flow Cytometry," *Cytometry* 14:862-875, 1993.

Weir et al., A Limited Antibody Panel can Distinguish B-Precursor Acute Lymphoblastic Leukemia from Normal B Precursors with Four Color Flow Cytometry:Implications for Residual Disease Detection, *Leukemia* 13:558-567, 1999.

Wells et al., "Occult B Cell Malignancies Can Be Detected by Three-Color Flow Cytometry in Patients with Cytopenias," *Leukemia* 12:2015-2023, 1998.

Wells et al., "Multidimensional Flow Cytometry of Marrow Can Differentiate Leukemic From Normal Lymphoblasts and Myeloblasts After Chemotherapy and Bone Marrow Transplantation," *Am. J. Clin. Path.* 110:84-94, 1998.

Wells et al., "Myeloid and Monocytic Dyspoiesis as Determined by Flow Cytometric Scoring in Myelodysplastic Syndrome Correlates with the IPSS and with Outcome After Hematopoietic Stem Cell Transplantation," *Blood* 102(1):394-403, Jul. 2003.

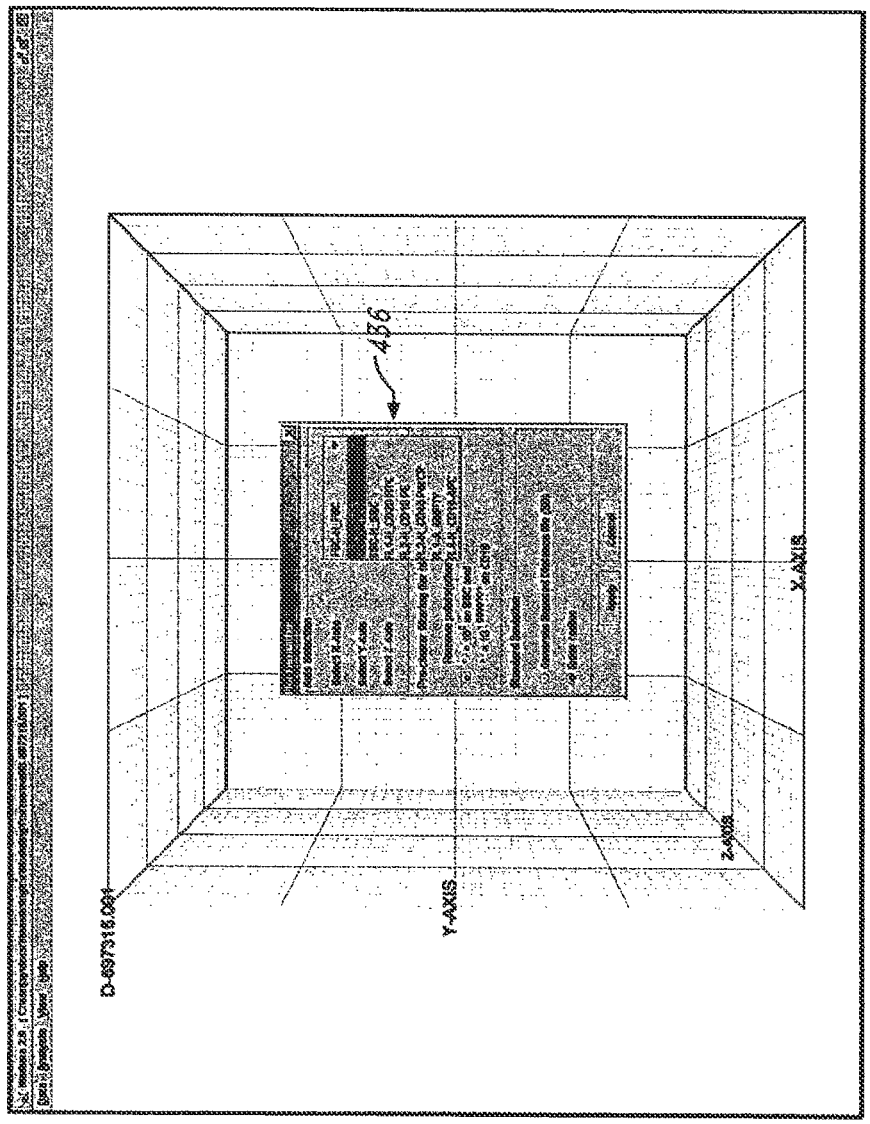

SYSTEM, METHOD, AND ARTICLE FOR DETECTING ABNORMAL CELLS USING MULTI-DIMENSIONAL ANALYSIS

BACKGROUND OF THE INVENTION

Field of the Invention

This invention is directed to multi-dimensional analysis of measured cell characteristics and in particular to a system, method and article for detecting abnormal cells in a test set of cells using multi-dimensional analysis of cell characteristics measured using flow cytometry.

Description of the Related Art

One method for characterizing heterogeneous cell populations is by flow cytometry, originally developed by Herzenberg and co-workers (*Science*. 1969 166(906):747-9; *J Histochem Cytochem*. 1976 24(1):284-91; *Clin Chem*. 1973 19(8):813-6; Ann. N.Y. Acad. of Sci. 1975 254:163-171). Using this technology, cells are labeled with antibodies conjugated to dyes. Flow cytometry can routinely detect 3, 4 or more immunofluorescent markers simultaneously in a quantitative manner. By combining multiple immunofluorescent labels with the light scattering properties of the cells it is possible to distinguish not only between cells of different lineages but between cells at various stages of maturation within those lineages. This is determined based on expression patterns of unique cell surface antigens (See for example, Loken M R, et al., in Flow Cytometry in Hematology. Laerum O D, Bjerksnes R. eds. Academic Press, New York, pp 31-42, 1992; Civin C I, et al., in "Concise Reviews in Clinical and Experimental Hematology" Martin J. Murphy ed. AlphaMed Press, Dayton Ohio, 1992, pp 149-159). Populations identified by the flow cytometer can then be isolated using the cell sorting electronics available on the instrument.

Multi-parameter flow cytometry is currently used to detect a variety of leukemias. However, current techniques require that time consuming data analysis be performed by a professional, namely someone well versed in both flow cytometry and hematopathology, such as a doctor. There is a long learning process required to educate a professional to make the distinction between normal and abnormal cell populations. In addition, when flow cytometry is used to monitor a patient's response to therapy, conventional techniques require the use of patient-specific panels for detecting residual disease.

Accordingly, there remains a need in the art for technology to improve accuracy of detection and simplify data analysis. The present invention may fulfill this and other needs.

BRIEF SUMMARY OF THE INVENTION

In one embodiment a normal set of cells is characterized using flow cytometry. A centroid and radius are defined for a set of clusters in an n-dimensional space corresponding to a normal maturation for a cell lineage in the normal set of cells. A test set of cells is characterized using flow cytometry and the characterization is compared to the set of clusters. This approach facilitates the detection of low levels of tumor cells based on their phenotypic differences from their normal counterparts as assessed by an analysis of complex data from normal and abnormal cell populations.

In one aspect, an embodiment comprises a method of diagnosing cancer in a test set of biological cells in an n-dimensional space, the method comprising: exposing each cell in a normal set of biological cells to a plurality of four or more reagents using a first protocol; measuring a corresponding plurality of fluorescence intensities of each cell in the normal set of biological cells using a second protocol; mapping each cell in the normal set of biological cells to a corresponding point in an n-dimensional space based at least in part on the measured plurality of fluorescence intensities of the cell in the normal set of biological cells, wherein the corresponding points form a normal set of points; defining a set of normal clusters in the n-dimensional space by defining a centroid line and radius based on the mapping of the normal set of points in the n-dimensional space, wherein each cluster in the set of normal clusters corresponds to a maturation level within a cell lineage; exposing each cell in a test set of biological cells to the plurality of reagents using the first protocol; measuring a corresponding plurality of fluorescence intensities of each cell in the test set of biological cells using the second protocol; mapping each cell in the test cell of biological cells to a corresponding point in an n-dimensional space based at least in part on the measured plurality of fluorescence intensities of the cell in the test set of biological cells, wherein the corresponding points form a test set of points; and comparing the test set of points to the set of normal clusters.

In one aspect, a method comprises exposing a cell to a plurality of any number of reagents. Some instruments are capable of producing nine or more colors. The use of increased reagents and colors facilitates the characterization of cells.

In another aspect, an embodiment comprises a method of characterizing a test set of biological cells in an n-dimensional space, the method comprising: mapping each cell in a normal set of biological cells to a corresponding point in an n-dimensional space using a first protocol, wherein the corresponding points form a normal set of points; defining a centroid and radius for a set of normal clusters in the n-dimensional space based on the mapping of the normal set of points in the n-dimensional space, wherein a cluster corresponds to a maturation level within a cell lineage; mapping each cell in a test set of biological cells to a corresponding point in the n-dimensional space using the first protocol, the corresponding points forming a test set of points; and comparing the test set of points to the set of normal clusters.

In another aspect, an embodiment comprises a method of diagnosing a test set of biological cells, the method comprising: mapping each cell in the test set of biological cells to a corresponding point in an n-dimensional space using a defined protocol, the corresponding points forming a test set of points; and comparing the test set of points to a defined set of normal clusters in the n-dimensional space, wherein a cluster in the defined set of normal clusters corresponds to a maturation level within a cell lineage and a cluster is defined by a centroid and radius.

In another aspect an embodiment comprises a method of characterizing a test set of biological cells, the method comprising: mapping each cell in the test set of biological cells to a corresponding point in an n-dimensional space using a defined protocol, the corresponding points forming a test set of points; representing the test set of points in a Cartesian coordinate display comprising a first axis corresponding to a cell maturation within a cell lineage and a second axis corresponding to a frequency of occurrence; and representing in the Cartesian coordinate display a set of normal clusters in the n-dimensional space, wherein a cluster is defined by a centroid and a radius and corresponds to a cell maturation level within a cell lineage.

In another aspect an embodiment comprises a method of characterizing a normal cell lineage in an n-dimensional space, the method comprising: exposing each cell in a normal set of biological cells to a plurality of reagents using a first protocol; measuring a corresponding plurality of characteristics of each cell in the normal set of biological cells using a second protocol; mapping each cell in the normal set of biological cells to a corresponding point in an n-dimensional space based at least in part on the measured plurality of characteristics of the cell in the normal set of biological cells, wherein the corresponding points form a normal set of points; and defining a centroid and radius for a set of clusters based on the mapping of the normal set of points in the n-dimensional space, wherein each cluster corresponds to a maturation level within the normal cell lineage.

In another aspect an embodiment comprises a computer readable media storing instructions for causing a diagnostic system to facilitate a detection of cancerous cells in a test set of biological cells by: retrieving a first set of data comprising indications of a plurality of three or more fluorescence intensities for each cell in a normal set of biological cells measured using a defined protocol; mapping each cell in the normal set of biological cells to a corresponding point in an n-dimensional space based at least in part on the first set of data, wherein the corresponding points form a normal set of points; defining a centroid line and radius for a set of normal clusters in the n-dimensional space based on the mapping of the normal set of points in the n-dimensional space, wherein a cluster corresponds to a maturation level within a cell lineage; retrieving a second set of data comprising indications of a corresponding plurality of fluorescence intensities for each cell in a test set of biological cells measured using the defined protocol; mapping each cell in the test cell of biological cells to a corresponding point in an n-dimensional space based at least in part on the second set of data, wherein the corresponding points form a test set of points; and comparing the test set of points to the set of normal clusters.

In another aspect an embodiment comprises a computer readable media storing instructions for causing a diagnostic system to facilitate a detection of cancerous cells in a set of biological cells by: retrieving a first set of data; defining a centroid line and radius for a set of normal clusters in an n-dimensional space based on the first set of data, wherein a cluster in the set of normal clusters corresponds to a normal maturation level within a cell lineage; retrieving a second set of data; and comparing the second set of data to the set of normal clusters.

In another aspect an embodiment comprises a computer readable media storing instructions for causing a control system to facilitate a diagnosis of cells in a test set of biological cells by: receiving a first set of data corresponding to a plurality of fluorescence intensities for a normal set of biological cells measured using a defined protocol; defining a set of normal clusters in a multi-dimensional space based on the first set of data, wherein a cluster is defined by a centroid line and radius and corresponds to a cell maturation level within a cell lineage; receiving a second set of data corresponding to indications of a corresponding plurality of fluorescence intensities for each cell in a test set of biological cells measured using the defined protocol; and comparing the second set of data to the defined set of normal clusters.

In another aspect an embodiment comprises a computer readable media containing a data structure for use in characterizing a test set of biological cells, the data structure comprising: a header section; a text section; and a data section, wherein the text section contains information regarding the data section and the data section contains information to define a centroid and radius for a set of normal clusters and wherein a cluster in the normal set of clusters corresponds to a normal maturation level within a cell lineage.

In another aspect an embodiment of a diagnostic system comprises: a controller; a memory; a data interface; a control interface; and a graphics engine, wherein the diagnostic system is configured to compare a test set of data to a set of normal clusters in an n-dimensional space defined by a centroid and radius, and wherein a cluster in the set of normal clusters corresponds to a normal maturation level within a cell lineage.

In another aspect an embodiment of a system for diagnosing a test set of cells comprises: means for defining a set of normal clusters corresponding to a normal cell lineage; and means for comparing the test set of cells to the set of normal clusters.

These and other aspects of the present invention will become apparent upon reference to the following detailed description and attached drawings. All cited references, patents, patent applications, etc., are incorporated herein in their entirety as if each was incorporated individually.

BRIEF DESCRIPTION OF THE DRAWINGS

FIGS. 4A to 9A and 4B to 9B are illustrations of multi-dimensional data projected into pseudo two-dimensional displays generated by a system, such as the system illustrated in FIG. 1.

FIGS. 11A and 11B illustrate a menu of a graphical user interface generated by a system, such as the system illustrated in FIG. 1.

FIGS. 12A to 17A and 12B to 17B are illustrations of multi-dimensional data projected into pseudo two-dimensional displays generated by a system, such as the system illustrated in FIG. 1.

DETAILED DESCRIPTION OF THE INVENTION

Figure 1:
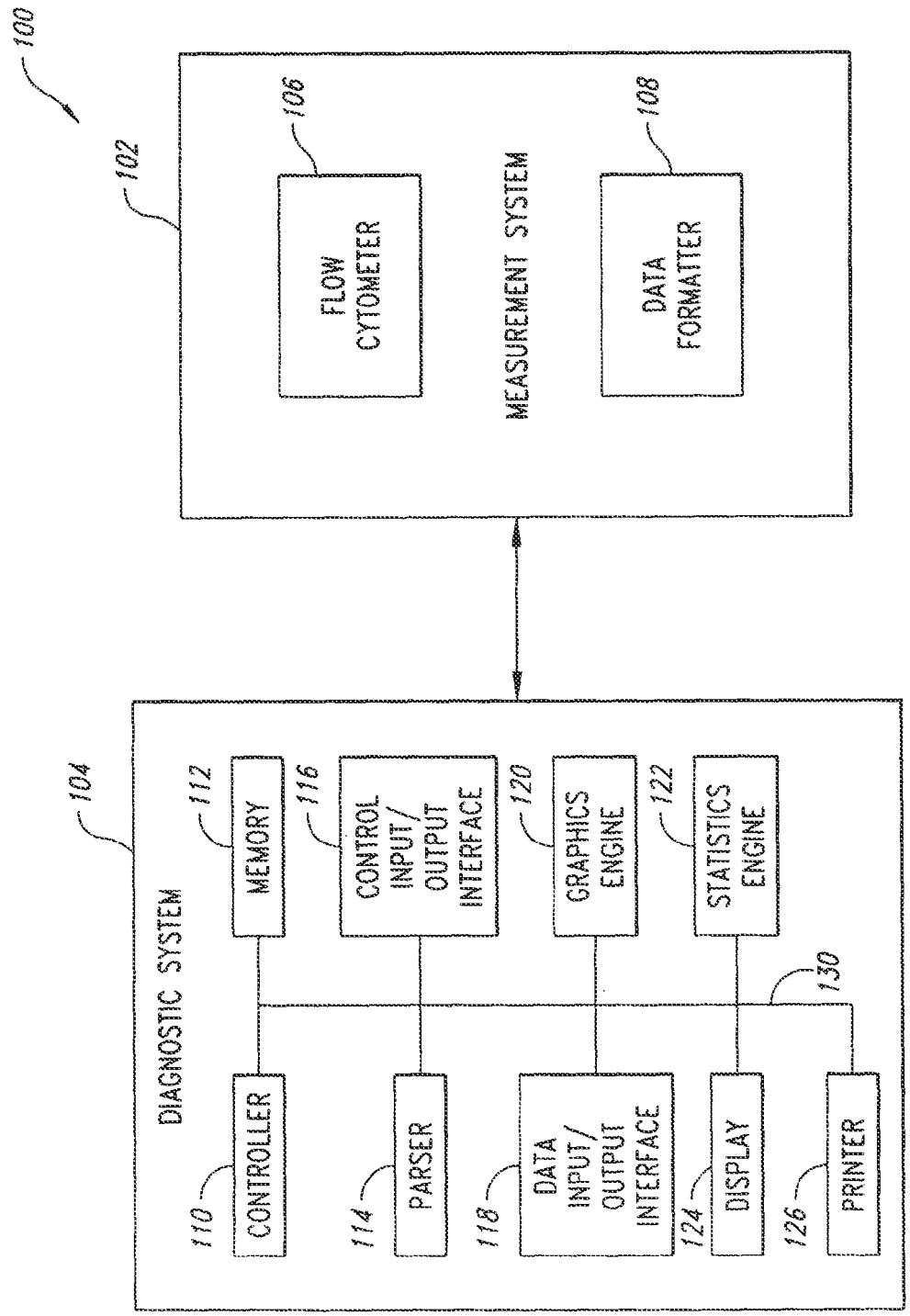
FIG. 1 is a functional block diagram of a system implementing an embodiment of a method of diagnosing a test set of cells.

Gene products can be identified on the cell surface or in the cytoplasm of cells using specific monoclonal antibodies. Flow cytometry can be used to detect multiple immunofluorescent markers simultaneously in a quantitative manner. The technique of immunofluorescent staining is well known and can be carried out according to any of a variety of protocols, such as those described in Current Protocols in Cytometry (John Wiley & Sons, NY, NY, Eds. J. Paul Robinson, et al.). Generally, a biological sample, such as peripheral blood, bone marrow, lymph node tissue, cord blood, thymus tissue, tissue from a site of infection, spleen tissue, tumor tissue, and the like, is collected from a subject and cells are isolated therefrom using techniques known in the art. In one embodiment, blood is collected from a subject and any mature erythrocytes are lysed using a buffer, such as buffered $NH_4Cl$. The remaining leukocytes are washed and then incubated with antibodies (e.g., monoclonal antibodies) conjugated to any of a variety of dyes (fluorophores) known in the art (see for example, http colon double slash www dot glenspectra dot co dot uk/glen/filters/fffluorpn dot htm or http colon double slash cellscience dot bio-rad dot com/fluorescence/fluorophoradata dot htm). Representative dyes in this context include, but are not limited to, FITC (Fluorescein Isothiocyante), R-phycoerythrin (PE), Allophycocyanin (APC), Cy7®, and Texas Red.

A wide variety of antibodies known in the art, and specific antibodies generated using techniques well known in the art, are useful in the context of the presently disclosed embodiments. Generally, the antibodies for use in the methods described herein are specific for a cell marker of interest, such as any of the CD cell surface markers (see for example the CD index at httpcolon double slash www dot ncbi dot nlm dot nih dot gov/PROW/guide/45277084 dot html; or Current Protocols in Immunology, John Wiley & Sons, NY, NY), cytokines, adhesion proteins, developmental cell surface markers, tumor antigens, or other proteins expressed by a cell population of interest. An antibody specific for virtually any protein expressed by a cell is useful in the context of the present disclosure. Illustrative antibodies include, but are not limited to antibodies that specifically bind to CD3, CD33, CD34, CD8, CD4, CD56, CD19, CD14, CD15, CD16, CD13, CD38, CD71, CD11 b, HLA-DR, glycophorin, CD45, CD20, CD5, CD7, CD2, CD10 and TdT.

After a period of incubation with a dye-conjugated antibody, typically about 20 minutes in the dark (incubation times and conditions may vary according to particular protocols), the leukocytes are washed with buffered saline and resuspended in buffered saline containing protein for introduction into a flow cytometer.

The flow cytometer analyzes the heterogeneous cell population one cell at a time and can classify the cells based on the binding of the immunofluorescent monoclonal antibody and the light scattering properties of each cell (see, for example, Immunol Today. 2000 21(8):383-90). Fluorescence detection is accomplished using photomultiplier tubes; the number of detectors (channels) determines the number of optical parameters the instrument can simultaneously examine while bandpass filters ensure that only the intended wavelengths are collected. Thus, flow cytometry can routinely detect multiple immunofluorescent markers in a quantitative manner and can measure other parameters such as forward light scatter (which is an indication of cell size) and right angle light scatter (which is an indication of cell granularity). Accordingly, a wide variety of cell populations can be differentiated and sorted using immunofluorescence and flow cytometry.

For example, by combining 4 colors of immunofluorescence with the physical parameters of forward light scatter (measure of cell size) and right angle light scatter (measure of cell granularity), a six dimensional data space can be generated wherein specific cell populations found in normal blood or bone marrow are restricted to small portions of the data space. As would be recognized by the skilled artisan after reviewing the specification, more or less than 4 colors of immunofluorescent markers could also be used. Excitation of fluorophores is not limited to light in the visible spectrum; several dyes, such as the Indo series (for measuring intracellular calcium) and the Hoechst series (for cell-cycle analyses) are excitable in the ultraviolet range. Thus, some instruments currently available in the art are configured with ultraviolet-emitting sources, such as the four-laser, 10-color Becton Dickinson LSR II. Further, using a commercially available fluorescence activated cell sorter, such as the FACSVANTAGE™ (Becton Dickinson, San Jose, Calif.), the EPICS® ALTRA™ (Beckman Coulter, Fullerton, Calif.) or the MOFLO® sorter (DakoCytomation, Inc., Carpinteria, Calif.) cell populations can also be sorted into purified fractions.

Gene expression observed during the development of blood cells from hematopoietic stem cells to mature cells found in blood is a highly regulated process. See Civin C I, Loken M R: *Cell Surface Antigens on Human Marrow Cells: Dissection of Hematopoietic Development Using Monoclonal Antibodies and Multiparameter Flow Cytometry*, Int'l J. Cell Cloning 5:1-16 (1987), which is incorporated herein by reference in its entirety. Thus, specific, tightly controlled expression of genes occurs within not only different lineages of blood cells but also during different stages of maturation within those lineages. See Loken, M R, Terstappen L W M M, Civin C I, Fackler, M J: *Flow Cytometry Characterization of Erythroid, Lymphoid and Monomyeloid Lineages in Normal Human Bone Marrow*, Flow Cytometry in Hematology, Laerum O D, Bjerksnes R. eds., Academic Press, New York, pp. 31-42 (1992), which is incorporated herein by reference in its entirety. Not only do these gene products appear and/or disappear at precise stages of maturation, but the amounts of these glycoproteins are regulated within very tight limits in normal cells. It has been shown that these antigenic relationships are established early in fetal development and are constant throughout adult life on blood cells that are undergoing constant turnover and replenishment. See LeBein T W, Wormann B, Villablanca J G, Law C L, Shah V O, Loken M R: *Multiparameter Flow Cytometric Analysis of Human Fetal Bone Marrow B Cells*, Leukemia 4:354-358 (1990), which is incorporated herein be reference in its entirety. These patterns and relationships of gene expression during maturation of normal cells are maintained following chemotherapy or even bone marrow transplantation. See Wells D A, Sale G E, Shulman H E, Myerson D, Bryant E, Gooley T, Loken M R: *Multidimensional Flow Cytometry of Marrow Can Differentiate Leukemic Lympho-* blasts From Normal Lymphoblasts and Myeloblasts Following Chemotherapy and/or Bone Marrow Transplant, Am. J. Clin. Path. 110:84-94 (1998), which is incorporated herein by reference in its entirety. Therefore, there is a very tightly coordinated regulation of multiple genes during normal development of blood cells both in terms of timing of expression as well as regulation of amounts of gene products expressed on the cell surfaces.

A comparison of normal antigen expression to neoplastic processes indicates that regulation of gene expression is disrupted in neoplastic cells. This disruption gives rise to different antigenic relationships than those observed during normal maturation of cells. See Hurwitz, C A, Loken M R, Graham M L, Karp J E, Borowitz M J, Pullen D J, Civin C I: *Asynchronous Antigen Expression in B Lineage Acute Lymphoblastic Leukemia*, Blood, 72:299-307 (1998). These are not new antigens, but are those normally expressed gene products that have lost the coordinated regulation found in normal cells. Both acute lymphoblastic leukemia ("ALL") and acute myeloblastic leukemia ("AML") express antigens abnormally. See Terstappen L W M M, Loken M R: *Myeloid Cell Differentiation in Normal Bone Marrow and Acute Myeloid Leukemia Assessed by Multi-Dimensional Flow Cytometry*, Anal. Cell Path. 2:229-240 (1990), which is incorporated herein by reference in its entirety. The types of abnormalities include:

(1) Lineage infidelity, defined as the expression of non-lineage antigens;

(2) Antigenic asynchrony, e.g., the expression on mature cells of antigens that normally appear on immature cells;

(3) Antigenic absence; and (4) Quantitative abnormalities.

See Terstappen L W M M, Konemann S, Safford M, Loken M R, Zurlutter K, Buchner Th, Hiddemann W, Wormann B: *Flow Cytometric Characterization of Acute Myeloid Leukemia, Part II. Phenotypic Heterogeneity at Diagnosis*, Leukemia 6:70-80 (1991), which is incorporated herein by reference in its entirety.

Not only are phenotypes of leukemic cells different from normal, the relationships between antigens are different from one case to the next, suggesting that each leukemic transformation causes a loss of coordinated gene regulation resulting in a unique phenotypic pattern for each leukemia. In 120 pediatric ALL cases and 86 adult AML cases each detailed phenotype was different from normal and from each other. See Id.; Hurwitz, supra. Thus, neoplastic transformation affects primary DNA sequence (genotype) and the regulation of normal genes so that they are inappropriately expressed at the wrong time during development, expressed in the wrong amounts, and/or are expressed in context with other genes that are not observed in normal cells (phenotype). The loss of coordinated gene regulation appears to be a hallmark of neoplastic transformation that results in abnormal phenotypes where each leukemic clone is different from normal and is different from other leukemias of the same type.

It should be noted that embodiments are not limited to the analysis of leukemic cells (e.g., acute and chronic lymphocytic leukemias (ALL, CLL) and acute and chronic myelogenous leukemia (AML, CML)) and other hematopoietic and lymphoid neoplastic cells. Embodiments can be applied to analysis of any of a variety of malignancies, e.g., lymphoma, myeloma or pre malignancies such as myelodysplasia, and other disorders, including any of a variety of hematologic disorders.

Flow cytometry can be adopted to use this phenotypic difference from normal to aid in the diagnosis of leukemia as well as in monitoring response to therapy. Flow cytometry has been used in hematopathology to phenotype the tumor, e.g., differentiating AML from ALL. However, conventional approaches require that the cells of interest form a predominant portion of the total cells examined and that the expected disease process be known before the analysis is performed, such as when a morphologic examination identifies a leukemic cell population of uncertain subtype. The focus on neoplastic cells can extend to residual disease detection. However, conventional residual disease detection techniques employing flow cytometry require a patient specific reagent panel to identify the specific phenotype observed at diagnosis. See Reading C I, Estey E H, Huh Y O, Claxton D F, Sanchez G, Terstappen L W, O'Brien M C, Baron S, Deisseroth A B, *Expression of Unusual Immunophenotype Combinations in Acute Myelogenous Leukemia*, Blood 81:3083-3090 (1993), which is incorporated herein by reference in its entirety. Such patient specific panels have been used to detect residual ALL and AML down to levels of 0.03-0.05%. See Coustan-Smith E, Sancho J, Hancock M L, Boyett J M, Behm F G, Raimondi S C, Sandlund J T, Rivera G K, Rubnitz J E, Ribeiro R C, Pui C H, Campana D, *Clinical Importance of Minimal Residual Disease in Childhood Acute Lymphoplastic Leukemia*, Blood 96:2691-2696 (2001); San Miguel J F, Vidriales M B, Lopez-Berges C, Diaz-Mediavilla J, Gutierrez N, Canizo C, Ramos F, Calmunitia M J, Perez J, Gonzalez M, Orfao A, *Early Immunophenotypical Evaluation of Minimal Residual Disease in Acute Myeloid Leukemia Identifies Different Patient Risk Groups and may Contribute to Postinduction Treatment Stratification*, Blood 98:1746-1751 (2002), which are incorporated herein by reference in their entirety.

Conventional detection of residual disease using patient specific reagent panels, however, suffers from the following limitations:

1. A diagnostic specimen with an aberrant phenotype is required in order to construct a panel. In 25% of cases an aberrant phenotype may not be identifiable. See Vidriales, supra.

2. Processing time is substantial because a technician must examine prior analysis for the particular patient in order to determine the reagent combination to use in each case.

3. The phenotype of a leukemic cell population that is different than the originally diagnosed phenotype may not be detected. For example, the phenotype may change from diagnosis to relapse as a result of clonal evolution or an outgrowth of a minor chemotherapy resistant subclone. See San Miguel, supra.

4. Unexpected or unanticipated abnormalities, such as secondary myelodysplasia or abnormalities in other lineages may be overlooked.

The assessment of residual disease using patient specific panels can work well in a controlled environment, such as a research study where there is access to all sequential specimens and there is high compliance in obtaining specimens at specific times in therapy. In clinical practice, however, a flow cytometry laboratory may be asked to perform residual disease analysis when the laboratory did not perform the initial diagnosis. A detailed immunophenotype is often unavailable or incomplete.

Residual disease detection can also be performed using standardized panels and difference from normal as the tumor specific marker. Coordinated gene expression is so precise that a divergence of ½ a decade in antigen expression is sufficient for the discrimination between normal and aberrant neoplastic cells. In such an approach, specific reagent panels are used for each suspected lineage, for example, B lineage ALL; T lineage ALL; AML; B lineage non-Hodgkins lymphoma ("B-NHL") and T lineage NHL ("T-NHL"), as well as MDS and myeloma. Tumor populations can be identified by first identifying patterns expected of normal cells, then focusing on cells that do not match the patterns expected of normal cells. This approach of detecting residual disease has been used by the Fred Hutchinson Cancer Research Center for several years and has been successful in predicting outcomes in hematopoietic neoplasms. For example:

1. In hematopoietic stem cell transplants for ALL, flow cytometry was shown to be more sensitive and more specific than morphology, cytogenetics, or the two technologies combined, in predicting relapse for 120 patients. See Wells, DA, supra.

2. In pediatric AML flow cytometric detection of residual disease was the best predictor of outcome in 252 patients studied. Sievers, E. L., Lange, B. J., Alonzo, T. A., Gerbing, R. B., Bernstein, I. D., Smith, F. O., Arceci, R. J., Woods, W. G., Loken, M. R., *Immunophenotypic evidence of leukemia after induction therapy predicts relapse: results from a prospective Children's Cancer Group study of 252 patients with acute myeloid leukemia*, Blood 101: 3398-3406 (2003). Patients with detectable tumor at any time during therapy were 4 times more likely to relapse and 3 times more likely to die than those patients in whom no tumor was detected.

3. In hematopoietic stem cell transplants flow cytometry is able to distinguish between normal regenerating blasts and recurrent tumor based on aberrant antigen expression. See Shulman H, Wells D, Gooley T, Myerson D, Bryant E, Loken M., *The biologic significance of rare peripheral blasts after hematopoietic cell transplant is predicted by multidimensional flow cytometry*, Am J Clin Path 112:513-523 (1999). Patients can exhibit 20% normal blasts in the blood or may have up to 50% regenerating blasts in the marrow without detection of neoplastic cells.

The detection of abnormal phenotypes of small populations of cells in blood or bone marrow extends the utility of flow cytometry to other applications beyond simply phenotyping leukemias. Flow cytometry has been used to show that a significant proportion (10%) of patients with a diagnosis of myelodysplasia have been misdiagnosed and have lymphoid, not myeloid abnormalities. See Wells D A, Hall M C, Shulman H E, Loken M R, *Occult B cell malignancies can be detected by three-color flow cytometry in patients with cytopenias*, Leukemia 12:2015-2023 (1998). Flow cytometry has also allowed the development of a scoring system to stratify patients with myelodysplasia based on the degree of abnormalities detected among the maturing myeloid cells. See Wells, D., Benesch, M, Loken, M., Vallejo, C., Myerson, D., Leisenring, W., Deeg, H., *Myeloid and monocytic dyspoiesis as determined by flow cytometric scoring in myelodysplastic syndrome correlates with the IPSS and with outcome after hematopoietic stem cell transplantation*, Blood 102: 394-403 (2003). The patients with myeloid cells that exhibited more aberrancies in gene expression as evidenced by abnormal immunophenotype, had a higher relapse rate and death post stem cell transplant as compared to patients with fewer detectable abnormalities. There was also a high correlation with the International Prognostic Scoring System (IPSS). In addition, a high flow cytometric score divided the Intermediate I group of patients in the IPSS system into statistically significant groups based on relapse post stem cell transplant.

There are several advantages of tumor detection based on difference from normal.

1. The technique does not require a diagnostic specimen for creation of a specific panel.

2. The approach allows for rapid processing of specimens in a high volume laboratory with identical panels being used for different patients.

3. The results are not affected by a change in phenotype following therapy.

4. Proper standardized panel selection permits the detection of unexpected or unanticipated findings that are the result of hematologic abnormalities.

Conventional distinction between normal and abnormal cell populations does have significant limitations. Data analysis conventionally must be performed by a professional (MD or PhD well versed in both flow cytometry and hematopathology) and not by a technician, since various clinical situations may indicate if abnormalities observed are normal or abnormal. There is a long learning process required to educate a professional to make the distinction between normal and abnormal cell populations. A well-trained hematopathologist may take 6 months to a year to learn the techniques. Currently, the assessment of normal against abnormal by the professional is based on experience with all the inherent difficulties of a subjective analysis, similar to the training in diagnostic microscopy. It is difficult to extend the analysis to other sites and maintain the same sensitivity and specificity. In difficult cases two or more professionals must come to a consensus for a final diagnosis.

For example, Weir, et al. describe a normal "template" resulting from four-color flow cytometric analysis of normal B cell precursors against which tumor samples can be compared. See Weir, E. G., et al., Leukemia (1999) 13:558-567. However, unlike the present invention, this template is a specific, fixed set of geometric regions drawn around the displayed dot plot events, which are then used as the boundaries of normal. As noted by Weir, et al., isolated events of uncertain nature present in normal samples that fall outside the template-defined boundaries of normal present a serious problem that has yet to be resolved with their method, particularly in the setting of minimal residual disease detection. Additionally, as with other prior methods, analysis by a highly trained individual is required to compare patient samples against the template.

In addition, the populations identified by multiple monoclonal antibodies in normal bone marrow are not distinct spherical clouds in multi-dimensional space. Rather, the data can be described as a series of tubes or snakes that change in size and position as lineages of cells traverse from immature to mature forms traveling from head to tail in the multi-dimensional data space. Thus, cluster analysis programs that treat data as spherical clouds, produce results with the limitations described above.

In contrast, the embodiments described further herein provide a method for determining, among other things, a centroid line and radius of one or more clusters of events corresponding to a normal cell maturation lineage. In this manner, statistical analysis can be used to determine whether an event represents an abnormal event (i.e., cancer).

Normal bone marrow is comprised of multiple lineages each undergoing continuous, steady state maturation. By first assessing normal cells, a statistical measure of what constitutes normal and what constitutes abnormal can be defined. This definition then becomes the standard for analysis. Automating the identification of which cells are within the expected, defined positions of normal will facilitate the teaching of new professionals and technicians as to what is phenotypically abnormal. It will also permit the standardization of analysis at multiple sites providing consistency between analysts in identifying abnormal populations.

Automating the identification of abnormal cells also allows for increased sensitivity. Current manual evaluation is performed using three antibodies in combination with forward and right angle light scatter collecting 10,000 events for each tube. A panel consists of between seven and fourteen different tubes each with a different combination of antibodies. Using this current system, tumors can be detected with specificity approaching 100%. See Am. J. Clin. Path. 110:84-94, supra; Blood 98:1746-1751, supra; Blood 101:3398-3406, supra. It is possible for a single professional to analyze and report between 20-30 such cases in a single day. Increasing sensitivity is a limitation under conventional approaches because the professional must spend more time analyzing each case. Automating the identification of abnormal cells will permit larger data sets (counting more cells) and application of more antibodies, without increasing the time an analyst must spend on each specimen.

The statistical analysis can be used to identify more subtle changes to hematopoietic abnormalities. This is especially important for analysis of Myelodysplastic Syndrome ("MDS"), where abnormalities are observed in the more mature cells rather than just the immature blasts. Statistical analysis will identify bulges in the tubes or shifts in the centroid line that may denote the abnormal regulation of cells. It may also define regulatory points and rates of progression through the developmental process, enabling a better understanding of the loss of coordinated gene regulation observed during neoplastic transformation.

FIG. 1 is a functional block diagram of a system 100 implementing an embodiment of a system for detecting abnormal cells using multi-dimensional analysis. The system 100 comprises a measurement system 102 and a diagnostic system 104.

The measurement system 102 measures characteristics of cells in a sample of cells, and as illustrated comprises a flow cytometer 106 and a data formatter 108. More than one flow cytometer 106 may be employed, although usually the measurements for a particular sample would be taken with one instrument. For example, as discussed in more detail below, measurements from a normal set of cells may be taken with one flow cytometer, while measurements from a test set of cells may be taken with another flow cytometer. Other measurement devices may be employed in the measurement system 102, such as a microscope (i.e., high throughput microscopy).

The measurement system 102 may contain a separate data formatter 108 to format the data collected by the measurement system 102. Alternatively, the data formatter 108 may be part of another component of the system 100, such as the flow cytometer 106 or the diagnostic system 104. The data formatter 108 may, for example, format data collected by a flow cytometer 106 into Flow Cytometry Standard FCS 2.0 format or another data file format. The measurement system 102 may comprise additional components, such as controllers, memories and/or circuitry and hardware.

The diagnostic system 104 analyzes data received from the measurement system 102, as discussed in more detail below. In the embodiment illustrated in FIG. 1, the diagnostic system 104 comprises a controller 110, a memory 112, a parser 114, a control input/output interface 116, a data input/output interface 118, a graphics engine 120, a statistics engine 122, a display 124, a printer 126 and a diagnostic system bus 130. The diagnostic system bus 130 may include a power bus, control bus, and status signal bus in addition to a data bus. For the sake of clarity, however, the various diagnostic system buses are illustrated in FIG. 1 as the diagnostic system bus 130.

The diagnostic system 104 may be physically remote from the measurement system 102. The measurement system 102 may be coupled to the diagnostic system 104 via one or more communication links, such as the Internet, an extranet, and/or an intranet or other local or wide area networks. Similarly, components of the diagnostic system 104 may be physically remote from one another and may be coupled together via communication links, such as the Internet, an extranet, and/or an intranet or other local or wide area networks. There may be one or more diagnostic systems each coupleable to one or more measurement systems.

The diagnostic system 104 may be implemented in a variety of ways, including as separate subsystems. The diagnostic system 104 may be implemented as a digital signal processor (DSP), an application-specific integrated circuit (ASIC), or the like, or as a series of instructions stored in a memory, such as the memory 112 and executed by a controller, such as the controller 110. Thus, software modifications to existing hardware may allow the implementation of the diagnostic system 104. Various subsystems, such as the parser 114 and the control input/output interface 116, are identified as separate blocks in the functional block diagram of FIG. 1 because they perform specific functions that will be described in more detail below. These subsystems may not be discrete units but may be functions of a software routine, which will probably, but not necessarily, be separately callable and hence identifiable elements. Any suitable software or combinations of software may be used to implement the diagnostic system 104, including, for example, WinList and/or Java implemented with a Java Run Time Environment or a 3-D Java Run Time Environment.

While the illustrated embodiment denotes a single controller 110, other embodiments may comprise multiple controllers. The memory 112 may comprise, for example, registers, read only memory ("ROM"), random access memory ("RAM"), flash memory and/or electronically erasable read programmable read only memory ("EEPROM"), and may provide instructions and data for use by the diagnostic system 104.

An embodiment of the invention is described herein with respect to a study that was conducted of the B lymphoid lineage. Where appropriate, references to FIG. 1 are incorporated into the description of the study. Embodiments described herein can be applied to study, characterize and diagnose other normal and diseased lineages, such as erythroid, T lymphoid and others, including those with multiple lineages, such as the myeloid lineages (see Shulman H, 1999, supra; Wells D A, 1998, supra; and Loken M R and Wells D A, *Normal Antigen Expression in Hematopoiesis: Basis for Interpreting Leukemia Phenotypes*, in Immunophenotyping, Eds Carleton Stewart and Janel K. A. Nicholson, 2000, Wiley-Liss, Inc.).

The B lymphocyte lineage is a single lineage and is well defined into 4 stages of development within the bone marrow with multiple antigenic differences between stages that have been well characterized. The entire B lineage is identified by the expression of a single antigen, CD19, permitting the detection of all 4 stages of B lineage cells. The earliest B lineage cells (Stage I) are identified by the expression of CD34, high levels of CD10 and low levels of CD45. During Stage II, CD34 is lost, CD10 intensity is reduced by a factor of 2, CD45 intensity increases and CD20 begins to be expressed. Once CD20 reaches a maximum, there is a further increase in CD45 with a loss of CD10 denoting Stage III. The final stage (IV) of B lymphoid development is characterized by the absence of CD10, expression of CD22 and high levels of CD45.

As would be understood by the skilled artisan, other cell lineages that can be characterized using the methods described herein may comprise multiple lineages or branched lineages and lineages may be defined into varying numbers of stages of development. For example, the myeloid lineage includes, among others, the erythroid and the granulocyte-monocyte lineage. The granulocyte-monocyte lineage branches into the monocyte and the neutrophil lineages.

Neutrophils can be divided into five identifiable stages. Stage I myeloblasts identified by the expression of CD34 also exhibit HLA-DR, CD13, and CD33 at high levels but do not express CD11 b, CD15, and CD16. These myeloblasts are intermediate in size by forward light scatter but have low SSC. The progression to stage II is denoted by the loss of CD34 and HLA-DR, acquisition of high levels of CD15, a dramatic increase in SSC expression, without expression of CD11 b (see Loken M R and Wells D A, 2000, supra). Stage II is accompanied by a slight decrease in CD33. Stage III of neutrophil development is marked by the acquisition of intermediate levels of CD11b, loss of CD13, and a decrease in SSC related to the appearance of secondary granules. Stage IV is noted by the correlated increase in CD13 and CD16 with a further slight decrease in CD33 expression. Stage V corresponds to the mature neutrophil found in peripheral blood. This cell has maximal amounts of CD16, CD13, and CD45 with an increase in density.

The monocyte lineage has three detectable stages based on the expression of cell surface antigens. Monocytic development has two stages of maturation after the myeloblast stage (indistinguishable from stage I of neutrophil development). These cells retain HLA-DR throughout their development, in contrast to the neutrophils that rapidly lose this antigen at the promyelocyte stage. The maturation of monocytes (stage II) is first identified by the rapid appearance of CD11b while maintaining intermediate levels of CD45. Stage II of monocyte development is accompanied by increases in CD13 and CD33 expression with low expression of CD15. Stage III of development is defined by a coordinated increase in both CD45 and CD14 (see Loken M R and Wells D A, 2000, supra).

Erythroid cells have only two stages (see Loken M, 1992, supra). Commitment to this lineage is identified by the loss of CD45 and increase in CD71, stage I. The expression of glycophorin and the appearance of hemoglobin mark the second stage. The final steps of maturation of the erythroid cells are observed by the loss of the nucleus, a decrease in CD71, and subsequent loss of RNA in the reticulocytes (see Loken, M R, Shah V O, Dattilio K L, Civin C I (1987) *Flow cytometric analysis of human bone marrow. I. Normal erythroid development*. Blood 69:255-263).

As described in Loken M R and Wells D A, 2000, supra, T-lymphoid cells can be divided into four stages of development in the thymus by the pattern of reactivity of 10 antigens (CD1a, CD2, CD3, CD4, CD5, CD7, CD8, CD10, CD34, and CD45). Three stages are clearly defined by multiple antigenic differences while the fourth is distinguished by size.

Thus, as would be understood by the skilled artisan upon reading the present description, the methods described herein using the B-lymphoid lineage as an example, can be used to characterize in an n-dimensional space other cell lineages such as those described herein and known in the art.

In the embodiment of the invention described herein with respect to the B lymphoid lineage, all four stages of B cell development were identified using two reagent tubes with four colors:

Tube 1: CD20 FITC, CD10 PE, CD45 PerCP and CD19 APC.

Tube 2: CD22 FITC, CD34 PE, CD45 PerCP and CD19 APC.

The redundancy of markers (CD19 and CD45) in both tubes allows for comparison of data between the different tubes. In the study, data sets were collected with 200,000 events on a FACS Calibur flow cytometer (Becton Dickinson, San Jose, Calif.). The procedures for sample preparation are standard and followed a fixed protocol. See Am. J. Clin. Path. 110:84-94, supra. List mode data from two phenotypically normal patients was collected in FCS format for analysis. Clusters identified by someone well versed in both flow cytometry and hematopathology, such as a doctor, were compared to those clusters identified by the diagnostic system 104 using clustering algorithms. Visual centers of the clusters identified by the professional were compared to those generated by the diagnostic system 104. The process is iterative, in that the user revised the identified clusters based on the results from the clustering algorithms and ran additional clustering algorithms using the revised cluster definitions.

A four-color analysis of a set of normal bone marrow B lymphoid cells in tube 1 was performed. Specimens were collected to obtain 200,000 events for analysis. The cells were placed in a tube and stained with the reagents CD20-fluorescein (FITC), CD10 phycoerythrin (PE), CD45 peridinin chlorophyll protein (PerCP), and CD19 allophycocyanin (APC). Characteristics of the exposed cells were measured using flow cytometry (see flow cytometer 106 of FIG. 1). A system, such as the system 100 illustrated in FIG. 1, measures and analyzes the sample using a combination of the data received from the measurements and input from a user, such as a professional or a technician, as discussed in more detail below.

Figures 2, 3:
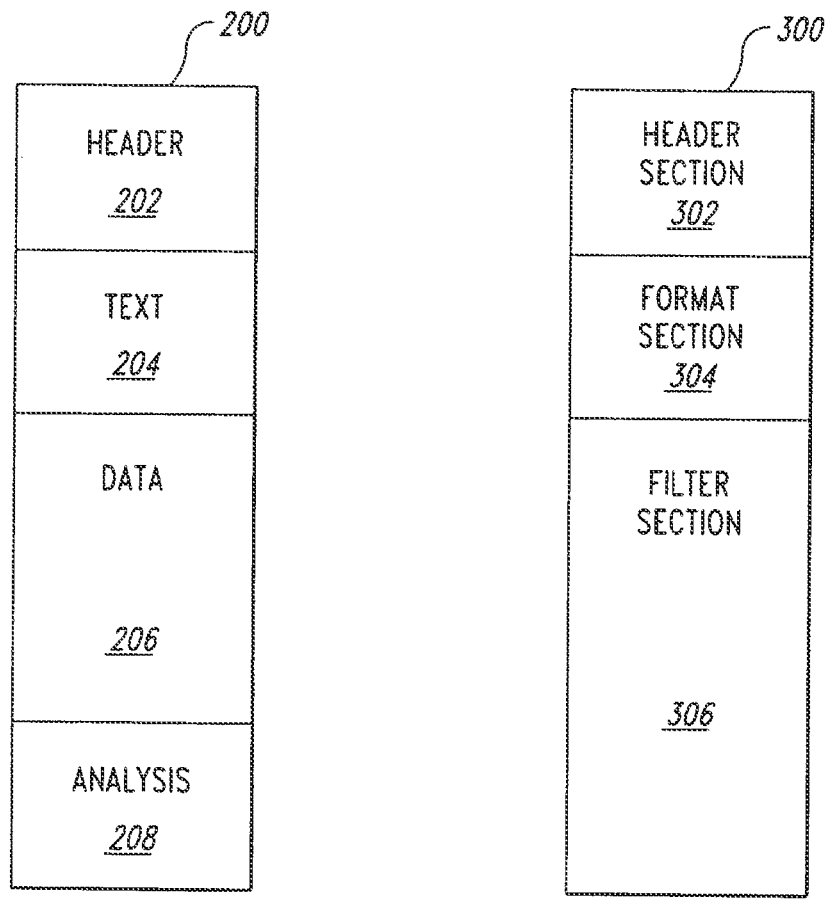
FIG. 2 is a schematic diagram of a data structure suitable for storing data related to a set of biological cells.
FIG. 3 is a schematic diagram of a data structure suitable for storing information related to processing of data contained in the data structure illustrated in FIG. 2.
Figure 4A:
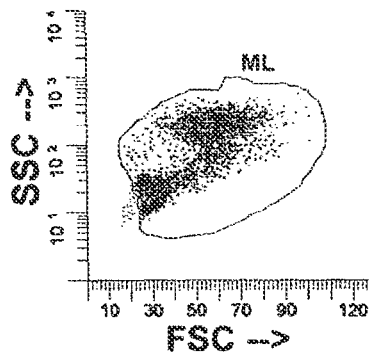

The publicly available Flow Cytometry Standard FCS 2.0 specification may be employed to store the measured characteristics of the cells in the samples. Other data formats and data structures may be employed, for example an FCS 1.0 or FCS 3.0 format may be employed. An example data structure 200 for storing a data set is illustrated in FIG. 2. With reference to FIGS. 1 and 2, the parser 114 parsed the header section 202, text section 204, data section 206 and analysis section 208 and collected information, including a parameter name, a total number of data points and data type details. The header section 202 describes the location of the other sections in the data structure 200. The header section 202 contains offset information of starting and ending points for the text 204, data 206 and analysis 208 sections. The text section 204 contains a series of ASCII encoded keyword-value pairs that describe various aspects of the data structure 200. For example, $TOT/5000/ is a keyword-value pair indicating that the total number of events in the file is 5000 and $PAR gives Total parameter number. The data section 206 contains raw data. Such data is usually in one of three modes (list, correlated or uncorrelated) described in the text section 204, by, for example, a $MODE keyword value. The data may be written to the data section 206, for example, in one of four formats (binary, floating point, double precision floating point or ASCII) described by a $DATATYPE keyword value. One common form of data storage is list mode storage in the form of binary integers ($DATATYPE/I/ $MODE/L/). The $PnB set of keywords may specify the bit width for the storage of each parameter. The PnR set of keywords may specify the channel number range for each parameter. For example, $PnB/16/$PnR/1024/, where n is an integer, may specify a 16-bit field for parameter n and a range for the values of parameter n from 0 to 1023, which corresponds to 10 bits. The analysis section 208 is an optional segment that, when present, may contain the results of data processing. The analysis can also be performed off-line, after the data has been collected and stored in a data structure, such as the data structure 200. In the test study, an analysis section 208 was not used. An analysis section 208, however, could be used to store information defining a centroid line and radius for a data set.

The data offsets of FCS 2.0 format are given in a properties file. An example properties file 300 is illustrated in FIG. 3. The properties file contains a header section 302, which contains information about how to read the properties file 300, a format section 304, which contains information about the format of the data structure 200, and a filter section 306, which contains information the parser 114 can use to filter data stored in the data structure 200. The parser 114 uses the information extracted from the properties file 300 to parse the loaded data structure 200. The properties file 300 can be readily modified to permit the use of various data file formats, such as various Flow Cytometry Standard formats.

The system 100 may use fluorescence intensity corresponding to CD19 as an initial gate. Thus all 200,000 cells in a 200,000-cell event list need not be assessed, only the CD19 positive cells (which include all B lineage cells) may be assessed. This enhances the statistics by increasing the number of B lineage cells to be analyzed without increasing the computational time required to distinguish the B lymphoid cells from the majority of other cells in the marrow. Without such a gate on the cells of interest, it may take computational times of 6-8 hours to identify clusters in the 200,000-cell event list. The proportion of immature B lymphoid cells (Stages I-III) averages less than 2% of all nucleated cells in a normal bone marrow. See Loken, M. R., Shah, V. O., Dattilo, K. L., Civin, C. L., *Flow Cytometry Analysis of Human Bone Marrow: II. Normal B Lymphoid Development*, Blood 70:1316 (1987). Therefore, by increasing the total counts to 200,000, and gating on the relatively infrequent CD19 positive cells, the cells of interest are analyzed while maintaining the entire data set and avoiding artifacts introduced by electronic gating for CD19 during data collection. In alternative embodiments, however, electronic gating for CD19 during data collection may be employed.

The populations of interest from an example normal data set collected as described above with respect to tube 1 are illustrated in FIGS. 4A to 9A as a series of four-color analysis displays, which were generated using WinList. The populations of interest can also be displayed in other ways, such as corresponding four-shade analysis displays, which are illustrated in FIG. 4B to 9B. FIGS. 4A to 9A and 4B to 9B are collectively referred to herein as FIGS. 4 to 9.

Clusters of events are initially identified in multiple 2 by 2 display projections of the 6 dimensional data (4 color and 2 light scatter parameters). The displays may be, for example, representations of the data in a Cartesian coordinate system. The display projections may be generated by the graphics engine 120 illustrated in FIG. 1. A user, such as someone well versed in both flow cytometry and hematopathology, identifies an ML region in a 2 by 2 display projection in a coordinate system with a horizontal axis corresponding to a forward light scatter and a vertical axis corresponding to side light scatter, as illustrated in FIG. 4.

Figure 5A:
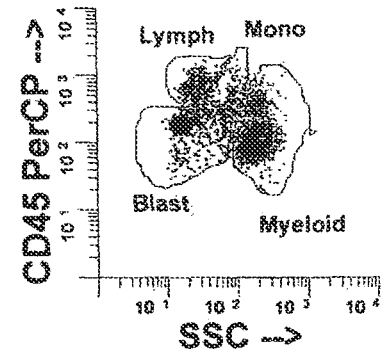
Figure 6A:
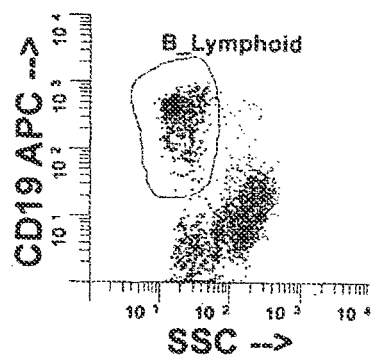
Figure 5B:
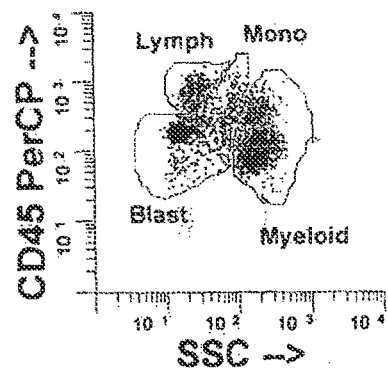
Figure 6B:
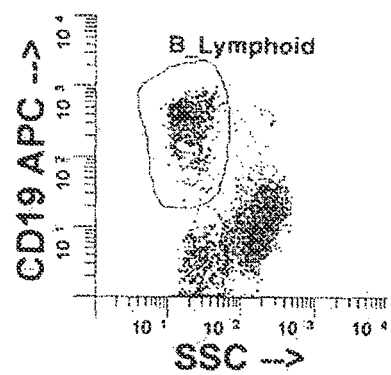

The ML region corresponds to nucleated cells. The user identifies lymphoid, monocyte, myeloid and blast regions in a 2 by 2 display projection in a coordinate system, such as a Cartesian coordinate system with a horizontal axis corresponding to a side light scatter and a vertical axis corresponding to a fluorescence intensity level for CD45, as illustrated in FIG. 5. The user identifies the B lymphoid cells in a 2 by 2 display projection in a coordinate system with a horizontal axis corresponding to side light scatter and a vertical axis corresponding to a fluorescence intensity level for CD19, as illustrated in FIG. 6.

Figure 7A:
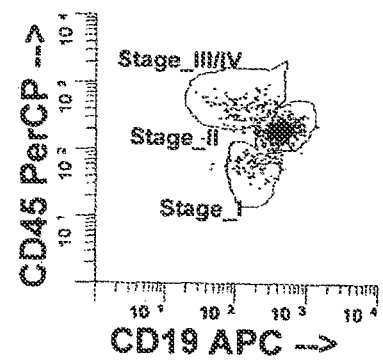
Figure 8A:
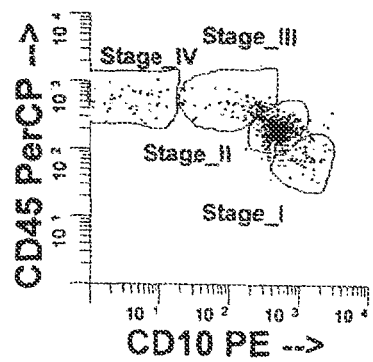
Figure 9A:
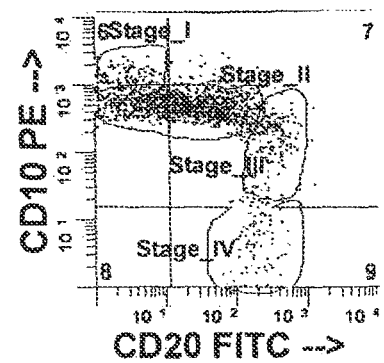
Figure 4B:
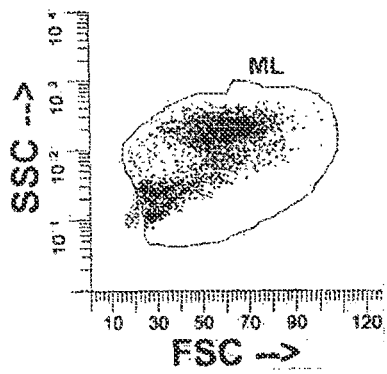
Figure 7B:
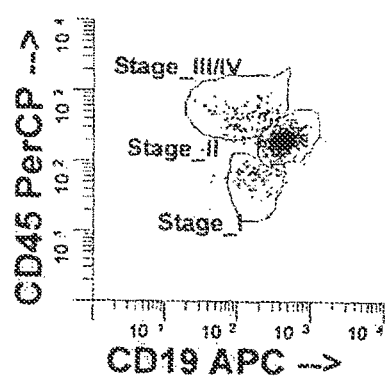
Figure 8B:
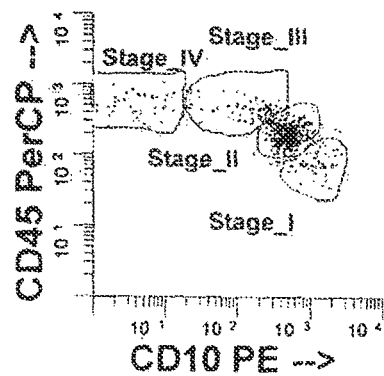
Figure 9B:
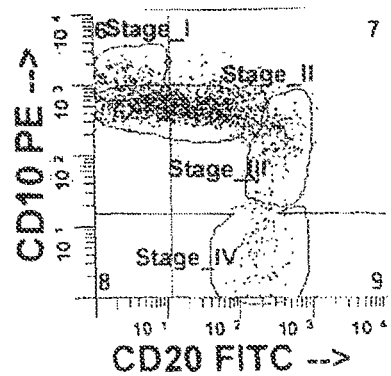

The user identifies a Stage I cluster, a Stage II cluster and a Stage III/IV cluster in a 2 by 2 display projection in a coordinate system with a horizontal axis corresponding to a fluorescence intensity level for CD19 and a vertical axis corresponding to a fluorescence intensity level for CD45, as illustrated in FIG. 7. The stages correspond to maturation levels for the B lymphoid cells. The user identifies a Stage I cluster, a Stage II cluster, a Stage III cluster and a Stage IV cluster in a 2 by 2 display projection in a coordinate system with a horizontal axis corresponding to a fluorescence intensity level for CD10 and a vertical axis corresponding to a fluorescence intensity level for CD45, as illustrated in FIG. 8. The user identifies a Stage I cluster, a Stage II cluster, a Stage III cluster and a Stage IV cluster in a 2 by 2 display projection in a coordinate system with horizontal axis corresponding to a fluorescence intensity level for CD20 and a vertical axis corresponding to a fluorescence intensity level for CD10, as illustrated in FIG. 9.

Based on the user's assessment of FIGS. 4-9, the accessed cells are assigned to an initial cluster. This results in a seven dimensional normal data set, the dimensions corresponding to: a forward light scatter; a side light scatter; a CD19 fluorescence intensity level; a CD45 fluorescence intensity level; a CD20 fluorescence intensity level; a CD10 fluorescence intensity level; and a cluster, corresponding to a stage of maturation within the B cell population. A color is assigned to each cluster identification and the data is mapped in a six dimensional space. The data is displayed by a diagnostic system, such as the diagnostic system 104 illustrated in FIG. 1, in a rotatable pseudo three-dimensional graphic display with color-coding based on cluster identification.

Figure 10A:
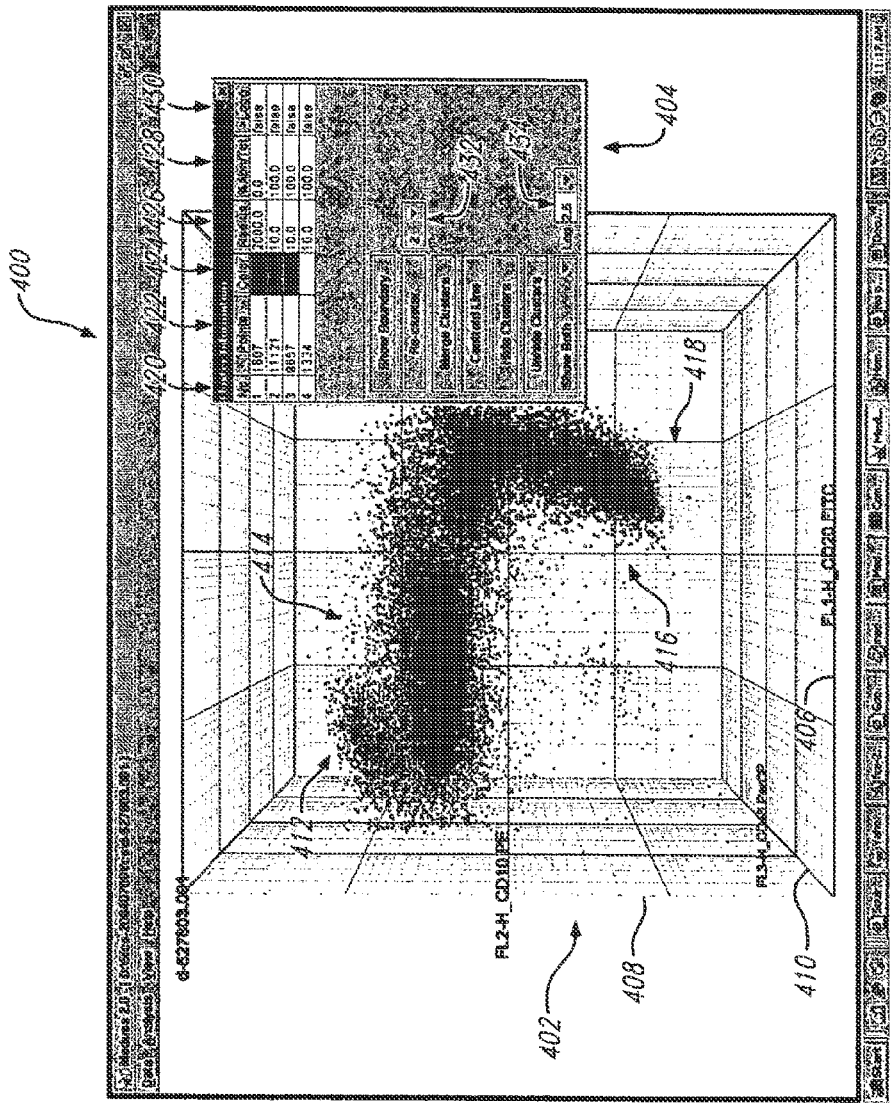
FIGS. 10A and 10B are illustrations of multi-dimensional data projected into pseudo three-dimensional displays generated by a system, such as the system illustrated in FIG. 1.
Figure 10B:
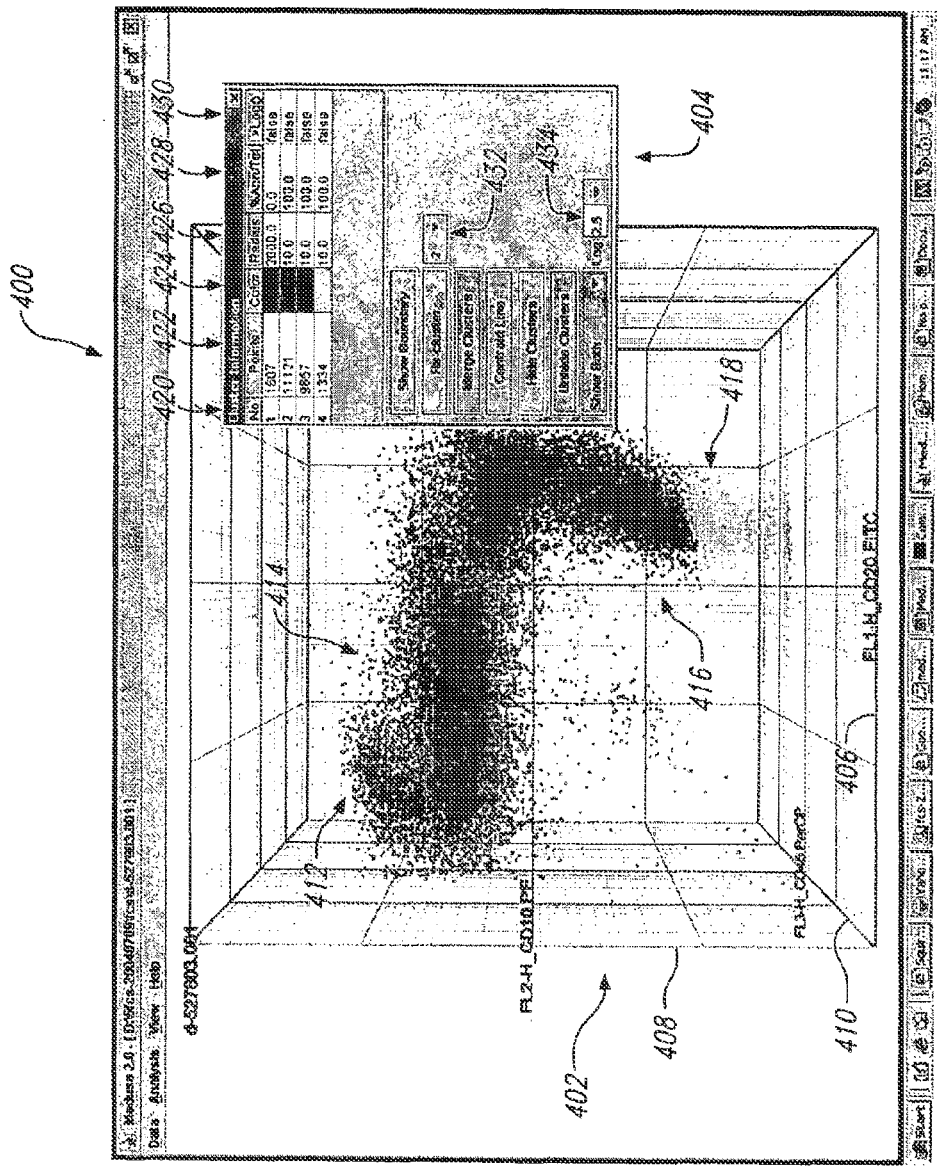

The diagnostic system 104 maps the normal data set to a three-axis coordinate system, such as a Cartesian coordinate system, and displays the data for viewing by the user. Each axis corresponds to one of the dimensions of the data set, with color indicating the cluster to which a particular cell is assigned. The data set can also be represented in a tabular display or in a combined display. FIGS. 10A and 10B (collectively FIG. 10) illustrate example displays 400 combining a pseudo 3-dimensional graphic representation 402 with a tabular representation 404. FIG. 10A is a color display and FIG. 10B is a corresponding shaded display.

The graphic representation 402 comprises an x-axis 406 corresponding to a fluorescence intensity for CD20, a y-axis 408 corresponding to a fluorescence intensity for CD10, and a z-axis 410 corresponding to a fluorescence intensity for CD45. Data in a first cluster 412 is assigned the color red and corresponds to a Stage I maturation level. Data in a second cluster 414 is assigned the color green and corresponds to a Stage II maturation level. Data in a third cluster 416 is assigned the color blue and corresponds to a Stage III maturation level. Data in a fourth cluster 418 is assigned the color yellow and corresponds to a Stage IV maturation level.

The tabular representation 404 comprises a first column 420 indicating a cluster number, a second column 422 indicating a number of points in the cluster, a third column 424 indicating the color or shade assigned to the cluster, a fourth column 426 indicating a radius of the cluster, a sixth column 428 indicating a percentage of abnormal events or points in the total set of events or points and a seventh column 430 indicating whether a logarithmic distance between the centroid point for a cluster and a statistical centroid point for the cluster is greater than a threshold value. The display 400 as illustrated may be an interactive computer display. The user can update information used to generate the display 400 using data entry fields 432, 434. As illustrated the threshold value is set at 2.5 in field 434.

Figure 11B:
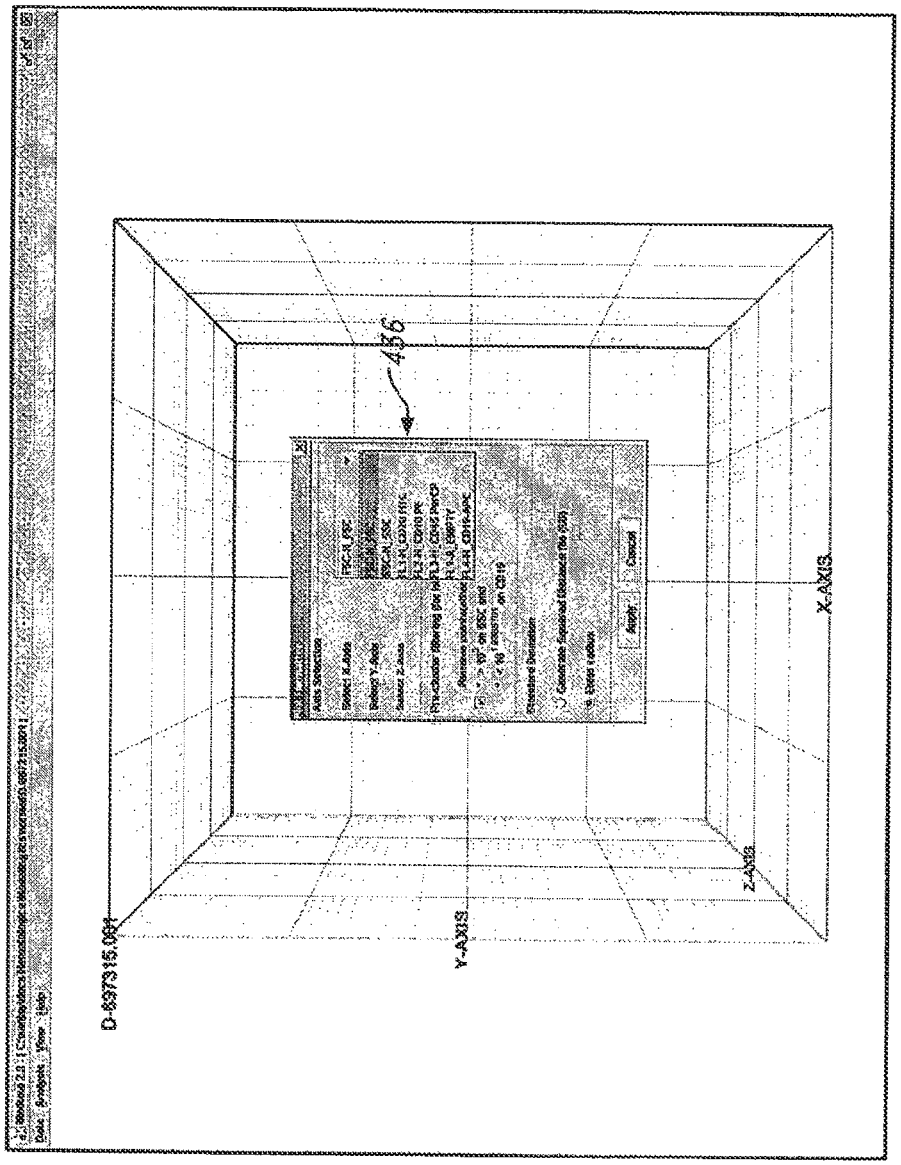

The diagnostic system 104 permits user selection of the three axes to which to map the data using a menu of a graphical user interface (GUI). FIGS. 11A and 11B illustrate an example menu 436 that can be employed by a diagnostic system, such as the diagnostic system 104 illustrated in FIG. 1. The diagnostic system 104 also permits user selection of other settings through menus. For example, menu selections may be included for: selecting between different stored filtering parameters, editing stored filtering parameters; and specifying new filtering parameter. For example, high-resolution data may be filtered to exclude data with a side scatter parameter corresponding to more that $10^2$ and a CD19 parameter corresponding to less than 10 to the 1.6989701. Menu selections also permit selection of a plane in the coordinate system on which to filter. Multiple filter criteria may be employed and the filter criteria can be greater than or less than specified thresholds. The menu system also allows selection of a specific cluster on which to apply various filter criteria. This allows the user to view various pseudo three-dimensional displays of the normal data set to assist the user in selecting initial data for use by the diagnostic system 104 in defining a centroid line and radius for the normal data set. The diagnostic system 104 also permits menu selection of a standard deviation method or fixed value and rotation of a displayed image. The diagnostic system 104 may also display cluster boundaries for a data set based on a selected centroid and radius.

The normal data set may also comprise separate data files corresponding to separate samples. For example, the user can examine and manipulate a data set comprising cells drawn from a single individual and a single tube, or the user can combine samples drawn from a plurality of individuals and/or tubes into a single normal data set. If a sample drawn from an individual is deemed to be abnormal, the sample can be excluded from the normal set of data.

Referring to the study, in the example B lymphoid data set from tube 1, the value n is equal to six. Each n-dimensional point is mapped to the n-dimensional space, which can be represented in a float array by n+1 float parameters. Table 1 illustrates the float array for an example six dimensional B lymphoid data set, where $P_1PR_1$ is the value of the first parameter for the first point, $P_2PR_1$ is the value of the first parameter for the second point, . . . $P_nPR_1$ is the value of the first parameter for the nth point, etc., with a seventh parameter added for a cluster to which a point is assigned, $P_nC\#$. The float array can be generalized for any number of dimensions. The diagnostic system 104 performs one or more selected clustering algorithms on the normal data set in n-dimensional space, refining the assignment of the points to a cluster.

TABLE 1

Float Array for Six Dimensional Data Set

| $P_1PR_1$ | $P_1PR_2$ | $P_1PR_3$ | $P_1PR_4$ | $P_1PR_5$ | $P_1PR_6$ | $P_1C\#$ |
|---|---|---|---|---|---|---|
| $P_2PR_1$ | $P_2PR_2$ | $P_2PR_3$ | $P_2PR_4$ | $P_2PR_5$ | $P_2PR_6$ | $P_2C\#$ |
| $P_3PR_1$ | $P_3PR_2$ | $P_3PR_3$ | $P_3PR_4$ | $P_3PR_5$ | $P_3PR_6$ | $P_3C\#$ |
| . . . | . . . | . . . | . . . | . . . | . . . | . . . |
| $P_nPR_1$ | $P_nPR_2$ | $P_nPR_3$ | $P_nPR_4$ | $P_nPR_5$ | $P_nPR_6$ | $P_nC\#$ |

The diagnostic system 104 allows the user to cluster the data using a selected clustering algorithm. For example, the user can specify a number of clusters, k, and use a K-means algorithm to cluster the data. For example, the diagnostic system 104 may divide the data into k clusters and assign a center to each cluster. The center can be assigned randomly to one of the points or entered based on observations by the user. The distance between two points in the n-dimensional space may be defined as follows:

$$D(P_1,P_2) = \text{SQRT}[(K_1(P_1PR_1 - P_2PR_1))^2 + (K_2(P_1PR_2 - P_2PR_2))^2 + (K_3(P_1PR_3 - P_2PR_3))^2 + \ldots + (K_n(P_1PR_n - P_2PR_n))^2]$$

Equation 1 where $D(P_1, P_2)$ is the distance between two points in the n-dimensional space and $P_1PR_1$ is the value of the first parameter for the first point, $P_2PR_1$ is the value of the first parameter for the second point, . . . $P_nPR_1$ is the value of the first parameter for the nth point, etc., and $K_1, K_2, K_3, \ldots K_n$ are weighting constants. In the study, the weighting constants were set equal to one. In other words, there was no weighting employed in the study. The centers may be iteratively updated until a convergence criteria is satisfied. In each iteration, each data point is assigned to its closest center, and the centers are recalculated using the mean parameter values of all points belonging to a cluster. Typical convergence criteria used in the study were no (or minimal) reassignment of points to new cluster centers. See Forgy, E, *Cluster Analysis of Multivariate Data: Efficiency vs. Interpretability of Classifications*, Biometrics, 21:768 (1965), for a discussion of k-means clustering.

Another example clustering algorithm is a DBSCAN clustering algorithm. A neighborhood radius, $E_{ps}$, and a threshold number of points in the neighborhood, minPts, are defined and the diagnostic system 104 employs a DBSCAN clustering algorithm. The neighborhood radius and threshold number of points are defined by the user. Density-based Clustering is based on the fact that clusters are of higher density than their surroundings. DBSCAN finds dense clusters automatically for a given density threshold. See Ester, M., Kriegel, H., Sander, J., Xu, X., *A Density-Based Algorithm for Discovering Clusters in Large Spatial Databases with Noise*, In Proceedings of 2d International Conference on KDD (1996), for a discussion of DBSCAN clustering. By definition the density threshold is specified by two parameters: neighborhood radius ($E_{ps}$) and threshold number of points in ϵ-neighborhood (minPts). A point 'p' is directly density-reachable from a point 'q', if 'p' is in the ϵ-neighborhood of 'q'. A point 'p' is density reachable from 'q', if there is a chain of points '$p_i$' where i=1 . . . n and '$p_{i+1}$' is directly density-reachable from '$p_i$', 'q' is '$p_1$' and 'p' is '$p_{i+1}$'. A point 'p' is density-connected to another point 'q', if there is a point 'o' such that both 'p' and 'q' are density-reachable from 'o'. In the study, the diagnostic system 104 started by bringing in a point to a temporary storage (tempStore, e.g. list) and finding its ϵ-neighborhood. If the ϵ-neighborhood of a data point contained less than 'minPts' points then it was marked as noise and another point was brought into tempStore. Otherwise, all ϵ-neighborhood points were brought into tempStore. The whole process was repeated until all points were considered. In short, DBSCAN clustering groups density-connected points together as a dense cluster and removes points that are not density-connected as noise.

The diagnostic system 104 may also employ, for example, bridge clustering to cluster the data. Bridge clustering combines K-means clustering with DBSCAN clustering. See Dash, M., Liu, H., Xu, X., '1+1>2': *Merging Distance and Density Based Clustering*, Proceedings of the IEEE 7th International Conference on Database Systems for Advanced Applications (DASFAA '01), Apr. 18-21, 2001, Hong Kong, China, for a discussion of bridge-clustering. K-means was performed first followed by density-based clustering over each k-means cluster, and at the end, k-means clusters were refined by removing the noise found in density-based clustering. For effective merging, each data point has the following three columns to store results of clustering: <k-means_ID>, <DBSCAN_ID> and <core/ϵ-core/non/core>, where:

K-means_ID is the cluster assigned to each point when k-means is run on the data points;

DBSCAN_ID is the cluster assigned to each point when DBSCAN is run on each k-means cluster; and core/ϵ-core/non-core values are assigned based on the following definitions:

Definition 1 (CoreDistance): For each cluster, CoreDistance is half of the distance between its center and its closest cluster center.

Definition 2 (CorePoint): It is not farther from its cluster center by 'CoreDistance-ϵ'. Core region of a cluster is that inside which each data point is core.

Definition 3 (+ϵ CorePoint): Its distance from cluster center is between 'CoreDistance' and 'CoreDistance+ϵ'.

Definition 4 (−ϵ CorePoint): Its distance from cluster center is between 'CoreDistance' and 'CoreDistance−ϵ'. For convenience, when +ϵ and −ϵ core points are considered, together they are denoted as ϵ-core. ϵ-core region is that in which each point is ϵ-core.

Definition 5 (Non-core point): It is neither a core nor an ϵ-core point. Non-core region is that in which each point is non-core.

The diagnostic system 104 can also employ wavelet clustering. Wavelet transforms are a special form of Fourier Transforms. See Press, W. H., Flannery, B. P., Teukiosky, S. A., *Numerical Recipes In C: The Art of Scientific Computing*, Ch. 13.10, Cambridge University Press (1992). This technique has been well established in the image processing and data mining areas for pattern and edge recognition. See Sheikholeslami, G., Chatterjee, S., Zhang, A., *WaveCluster: A Multi-Resolution Clustering Approach for Very Large Spatial Databases*, Proceedings of the 24th VLDB Conference, New York, USA, 1998. For example, the standard Daubechies wavelet filtering and the N-Dimensional Discrete Wavelet Transform (NDDFT) may be employed.

Figure 12A:
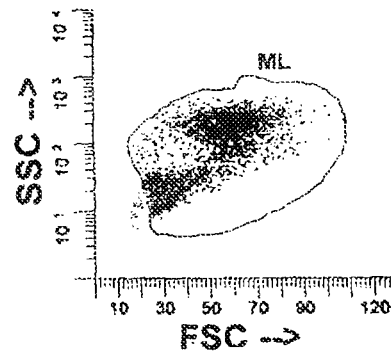
Figure 13A:
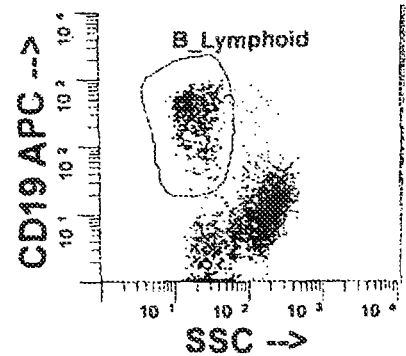
Figure 12B:
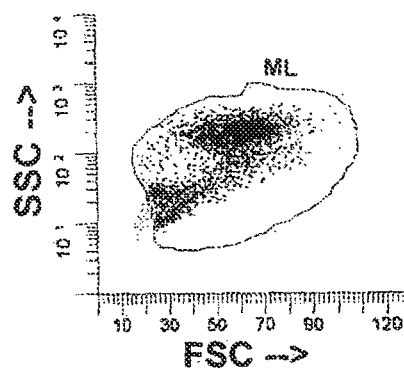
Figure 13B:
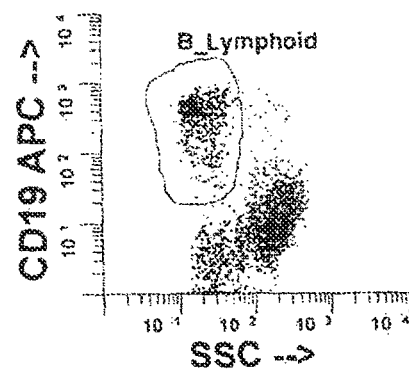

In a similar manner, the same populations (Stages) in a second normal data set are identified in the second tube (CD22, CD34, CD45, CD19), as illustrated in color in FIGS. 12A to 17A and in shading in FIGS. 12B to 17B (collectively referred to herein as FIGS. 12 to 17). The user identifies an ML region in a 2 by 2 display projection in a coordinate system with a horizontal axis corresponding to a forward light scatter and a vertical axis corresponding to side light scatter, as illustrated in FIG. 12. The ML region corresponds to nucleated cells. The user identifies B-lymphoid cells in a 2 by 2 display projection in a coordinate system with a horizontal axis corresponding to side light scatter and a vertical axis corresponding to a fluorescence intensity level for CD19, as illustrated in FIG. 13.

Figure 14A:
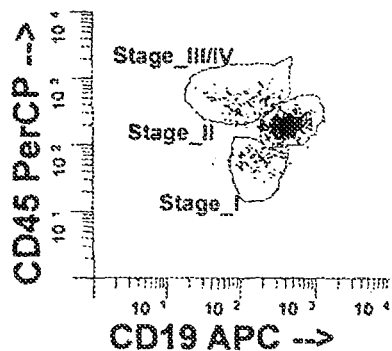
Figure 15A:
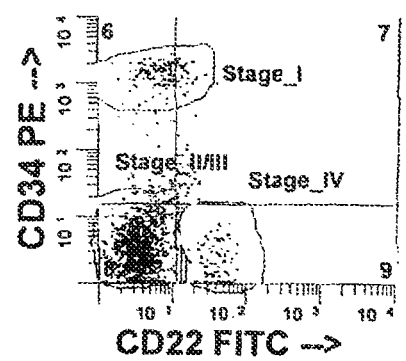
Figure 16A:
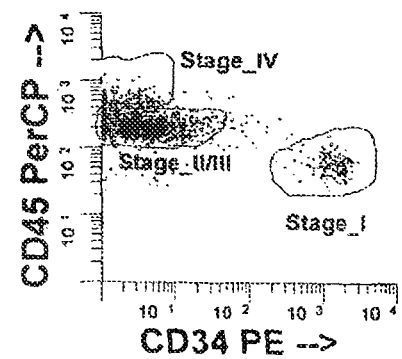
Figure 17A:
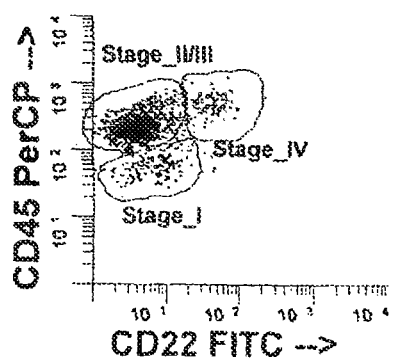
Figure 14B:
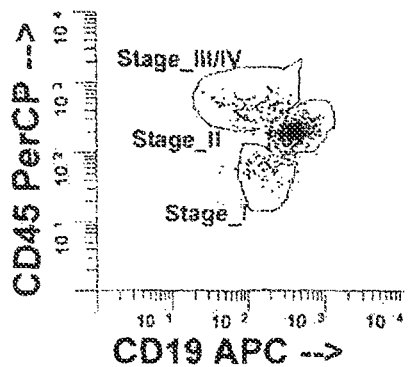
Figure 15B:
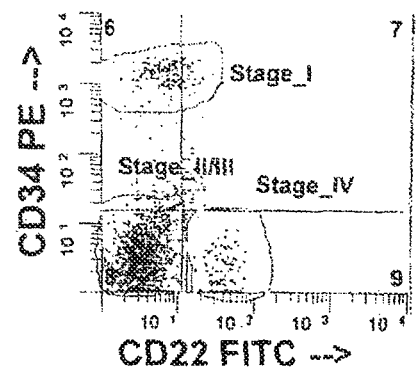
Figure 16B:
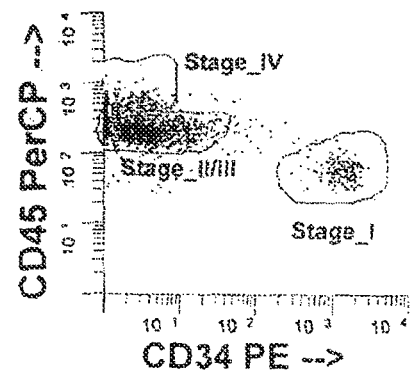
Figure 17B:
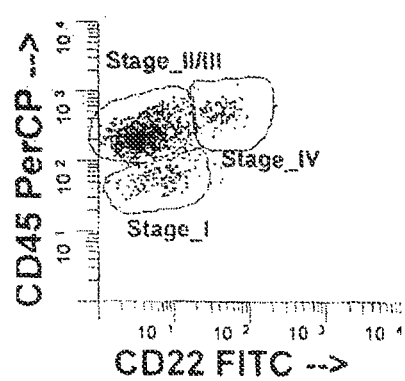

The user identifies a Stage I cluster, a Stage II cluster and a Stage III/IV cluster in a 2 by 2 display projection in a coordinate system with a horizontal axis corresponding to a fluorescence intensity level for CD19 and a vertical axis corresponding to a fluorescence intensity level for CD45, as illustrated in FIG. 14. The stages correspond to maturation levels for the B lymphoid cells. The user identifies a Stage I cluster, a Stage II/III cluster and a Stage IV cluster in a 2 by 2 display projection in a coordinate system with a horizontal axis corresponding to a fluorescence intensity level for CD22 and a vertical axis corresponding to a fluorescence intensity level for CD34, as illustrated in FIG. 15. The user identifies a Stage I cluster, a Stage II/III cluster and a Stage IV cluster in a 2 by 2 display projection in a coordinate system with horizontal axis corresponding to a fluorescence intensity level for CD34 and a vertical axis corresponding to a fluorescence intensity level for CD45, as illustrated in FIG. 16. The user identifies a Stage I cluster, a Stage II/III cluster and a Stage IV cluster in a 2 by 2 display projection in a coordinate system with a horizontal axis corresponding to a fluorescence intensity for CD22 and a vertical axis corresponding to a fluorescence intensity for CD45, as illustrated in FIG. 17. The results from Tube 1 and Tube 2 are combined to produce a single normal data set, as described in more detail below.

Figure 18A:
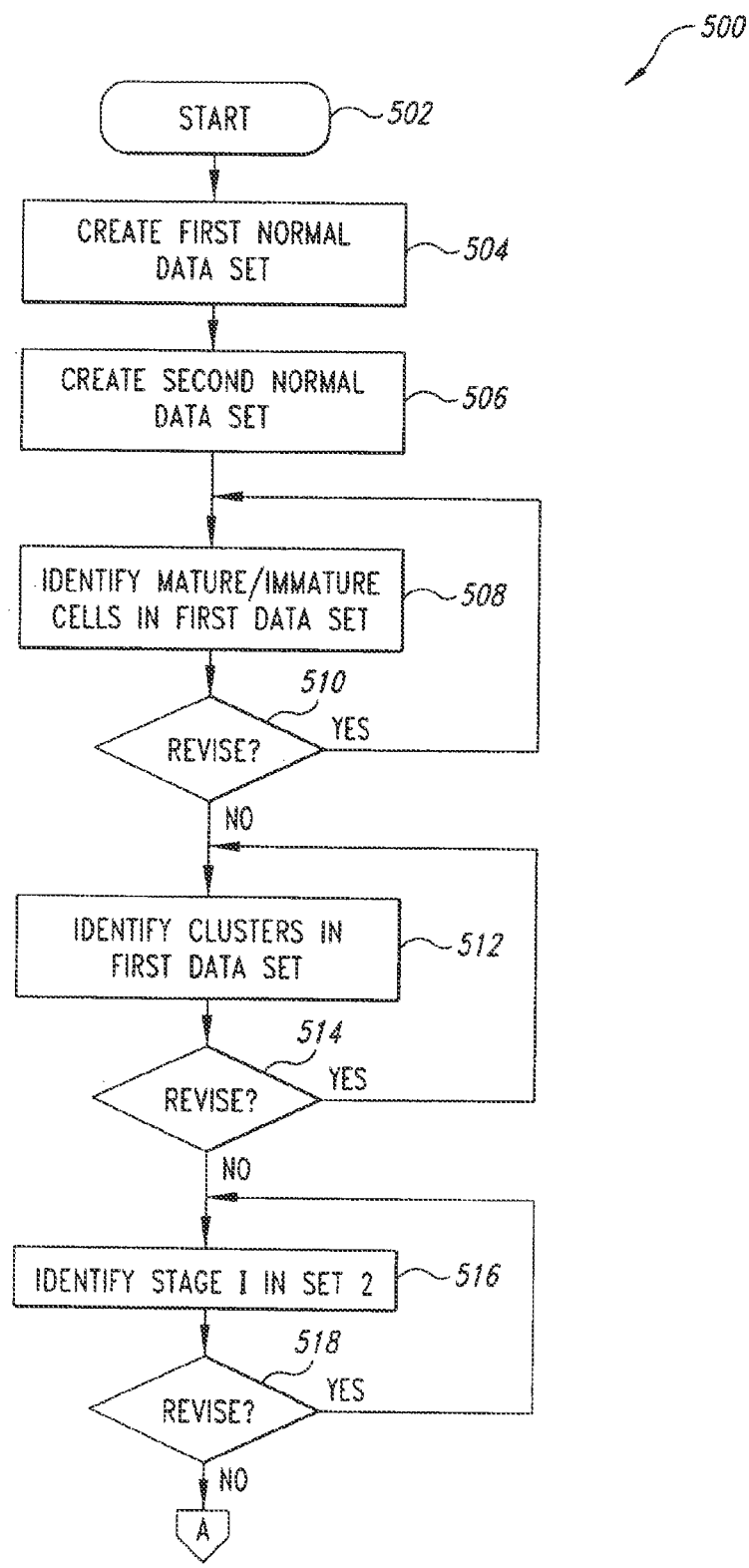
FIGS. 18A to 18C are a flow chart illustrating operation of a system to define a normal centroid and radius for a set of normal clusters corresponding to a normal cell lineage.
Figure 18B:
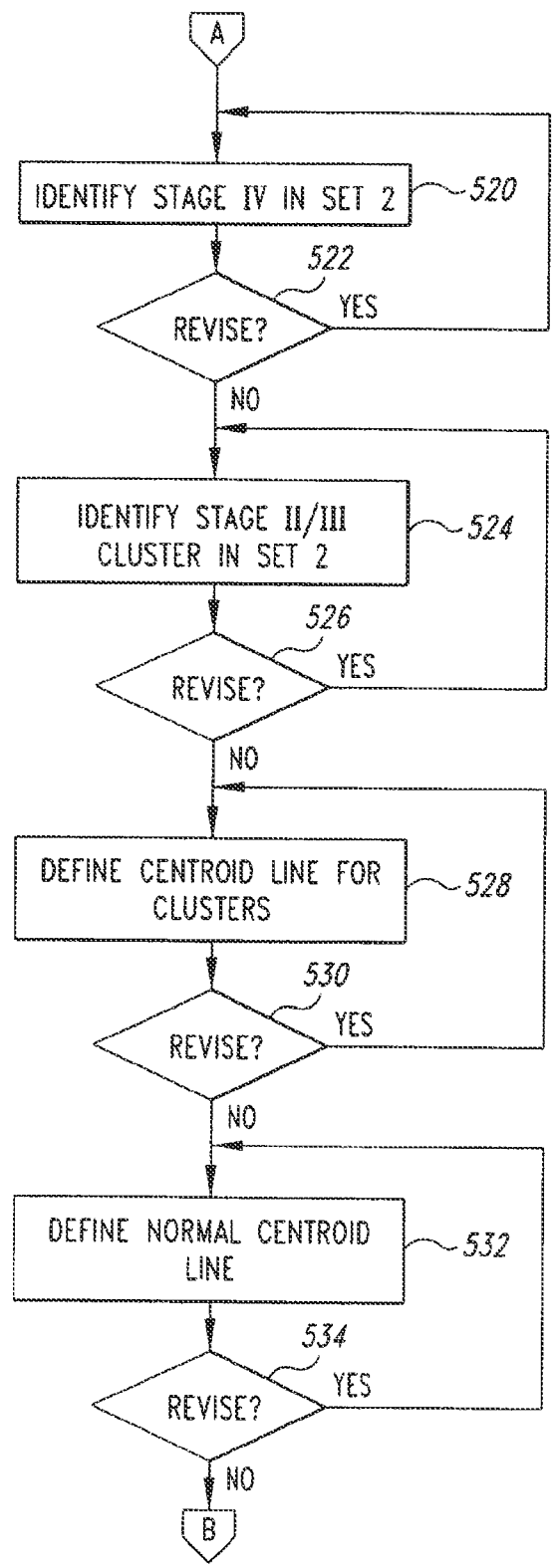
Figure 18C:
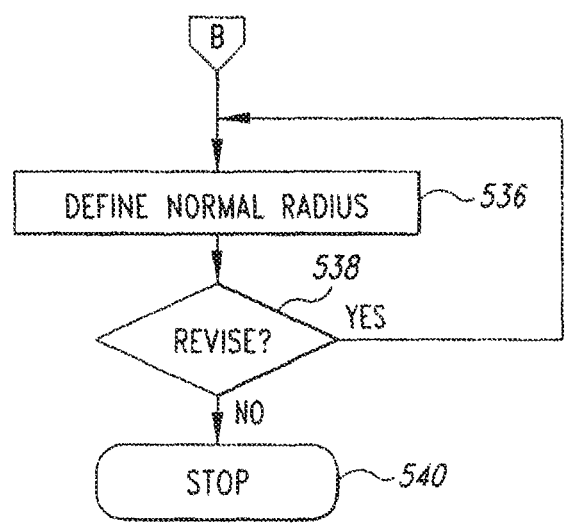

Once the clusters are identified and refined by the user selectively using the clustering software, a centroid line and radius are defined for the normal clusters, where each cluster corresponds to a cell maturation level within a cell lineage. FIGS. 18A to 18C illustrate an embodiment of a subroutine 500 that can be employed to define a normal population of cells, discussed with respect to the system 100 illustrated in FIG. 1 and the B lymphoid cells collected in tubes 1 and 2 as discussed above. The entire process of defining a normal population of cells should be viewed as an iterative one. Other cell lineages, such as a myeloid lineage, may comprise multiple lineages or branched lineages. In such cases, the multiple centroid lines may be defined or a defined centroid line may have branches.

The subroutine 500 starts at 502 and proceeds to 504. At 504, the system 100 filters a data set gathered by measuring characteristics of the cells in tube 1 by gating on CD19 positive cells, creating a first normal data set, and proceeds to 506. At 506, the system 100 filters a data set gathered by measuring characteristics of the cells in tube 2 by gating on CD19 positive cells, creating a second normal data set, and proceeds to 508.

At 508, the system 100 distinguishes between mature and immature cells in the first data set. This can be done by, for example, plotting fluorescence intensities for CD45 against fluorescence intensities for CD19 and clustering the first data set based on input from the user together with automated clustering techniques. The system proceeds to 510, where it determines whether to revise the distinction between the mature and immature cells in the first data set. This decision may be based on the results of automated clustering techniques, statistical analysis of the data, and/or displays of the data set generated based on the distinction, and may be automated and/or based on input from the user. If the system 100 determines the distinction should be revised, the system 100 returns to 508. If the system 100 determines the distinction should not be revised, the system proceeds to 512.

At 512, the system 100 identifies clusters representing Stages I, II, III and IV in the first data set. This can be done by, for example, plotting fluorescence intensities for CD45 against fluorescence intensities for CD10 and CD20 and clustering the data based on input from the user together with automated clustering techniques. The system 100 proceeds to 514, where it determines whether to revise the identification of the clusters in the first data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 512. If the system 100 determines the identification should be accepted, the system proceeds to 516.

At 516, the system 100 identifies a cluster representing Stage I in the second data set. This can be done by, for example, plotting fluorescence intensities for CD34 against fluorescence intensities for CD45 and clustering the data based on input from the user together with automated clustering techniques. The system proceeds to 518, where it determines whether to revise the identification of the Stage I cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 516. If the system 100 determines the identification should be accepted, the system proceeds to 520.

At 520, the system 100 identifies a cluster representing Stage IV in the second data set. This can be done by, for example, plotting fluorescence intensities for CD22 against fluorescence intensities for CD34 and clustering the data based on input from the user together with automated clustering techniques. The system proceeds to 522, where it determines whether to revise the identification of the Stage IV cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 520. If the system 100 determines the identification should be accepted, the system proceeds to 524.

At 524, the system 100 identifies a cluster representing Stages II and III in the second data set. This can be done by, for example, plotting fluorescence intensities for CD34 against fluorescence intensities for CD45 based on input from the user together with automated clustering techniques. The system proceeds to 526, where it determines whether to revise the identification of the Stage II/111 cluster in the second data set. This decision may be based on the results of the automated clustering techniques, statistical analysis of the data, and/or displays of the data set generated based on the identification, and may be automated and/or based on input from the user. If the system 100 determines the identification should be revised, the system 100 returns to 524. If the system 100 determines the identification should be accepted, the system proceeds to 528.

At 528, the system 100 defines a centroid line for each cluster identified at acts 512, 516, 520 and 524. A centroid line for a cluster may be fractal and may be determined based on input from the user together with automated clustering techniques. A centroid line for a cluster may be defined by, for example, combining the geometric mean in n-dimensional space with the centroid point determined by the clustering algorithms. The system proceeds to 530, where it determines whether to revise the defined centroid lines for the identified clusters. This decision may be based on the results of automated clustering techniques, statistical analysis of the data, and/or displays of the data set generated based on the identification, and may be automated and/or based on input from the user. If the system 100 determines the identification should be revised, the system 100 returns to 528. If the system 100 determines the identification should be accepted, the system proceeds to 532.

At 532, the system 100 defines a normal centroid line corresponding to a normal maturational lineage based on the combined data sets. This may be done by, for example, joining the defined centroid lines of the identified clusters using geometric bending. The system 100 also may combine input from the user with automated clustering techniques to define the normal centroid line. The distance along this centroid line as compared to the beginning and end is a measure of maturation of those cells for a given lineage as assessed by the specific combination of monoclonal reagents. It should be noted that different antibody combinations may be used to expand certain parts of the maturational process, while other combinations focus on other maturational stages or other lineages.

The system proceeds to 534, where it determines whether to revise the definition of the normal centroid line. This decision may be based on the results of automated clustering techniques, statistical analysis of the data, and/or displays of the data set generated based on the identification, and may be automated and/or based on input from the user. If the system 100 determines the definition should be revised, the system 100 returns to 532. If the system 100 determines the definition should be accepted, the system proceeds to 536.

At 536, the system 100 defines a boundary, or normal radius, around the defined normal centroid line. The normal radius, or boundary, may be a fixed radius, or it may vary. For example, it may be a fixed distance, such as 10, or it may be a function of a position on the defined normal centroid line or in the n-dimensional space. One definition may be employed for a first portion of the defined normal centroid line and a second definition may be employed for other portions of the defined normal centroid line. The normal radius may be determined using statistical algorithms, such as wavelet clustering techniques and/or K-means edge envelope techniques (using density of clusters) and/or be based on input from the user. Smoothing algorithms for defining specific 3-dimensional patterns may also be employed and compared against observations for a statistically determined number of files.

The system 100 proceeds to 538, where it determines whether to revise the defined normal radius. This decision may be based on the results of automated clustering techniques, statistical analysis of the data, and/or displays of the data set generated based on the identification, and may be automated and/or based on input from the user. If the system 100 determines the definition should be revised, the system 100 returns to 536. If the system 100 determines the definition should be accepted, the system proceeds to 540, where the subroutine 500 stops.

In some embodiments a system 100 may perform other acts not shown in FIGS. 18A to 18C, may not perform all of the acts shown in FIGS. 18A to 18C, or may perform the acts of FIGS. 18A to 18C in a different order. For example, the subroutine may be made more iterative. For example, the subroutine 500 may be modified so that the system 100 determines after act 538 whether to revise the defined normal centroid line, and if so, returns to 532. The subroutine 500 may also call other subroutines to perform various functions, such as the subroutine 600 described below with respect to FIG. 19. The subroutine 500 may also return the value of any desired variables, such as data entered by a user.

Figure 19:
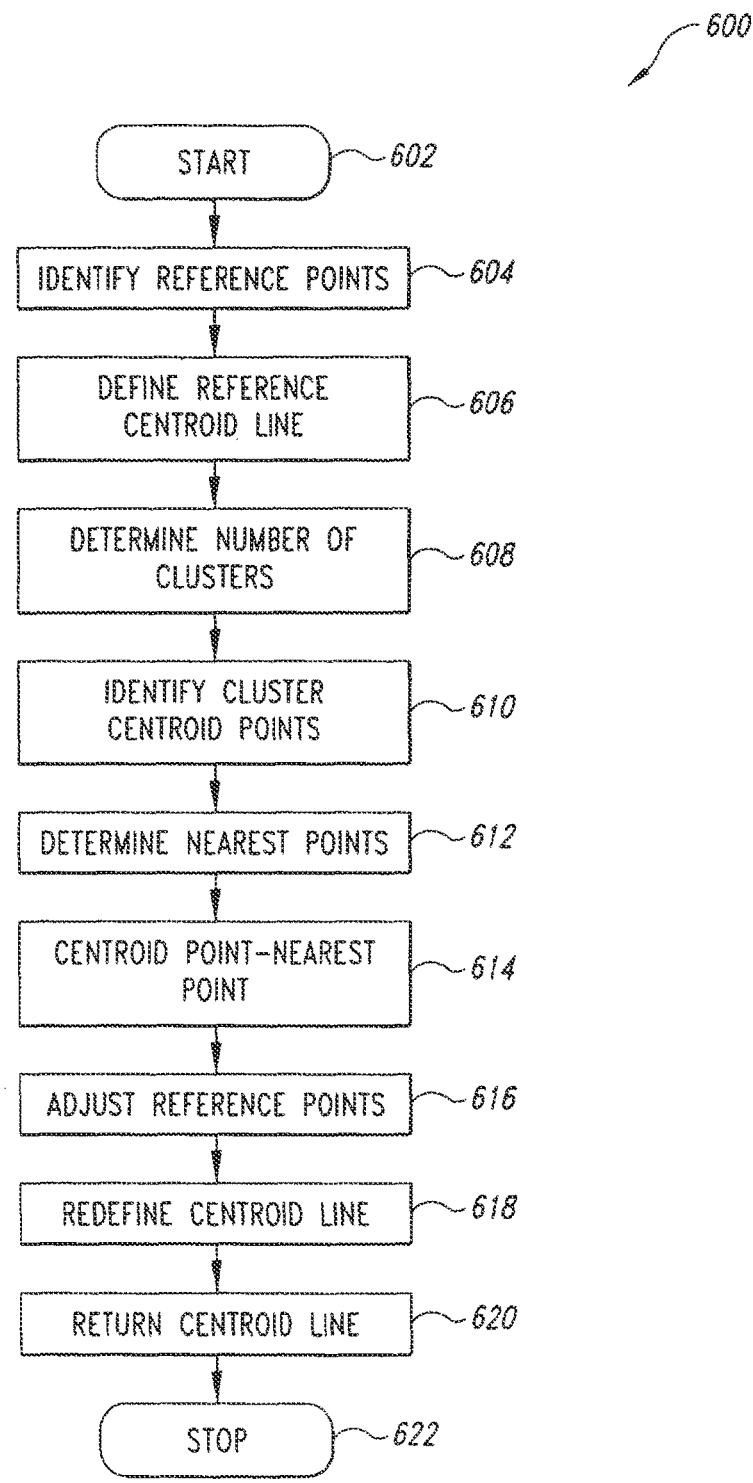
FIG. 19 is a flow chart illustrating operation of a system to define a centroid line for a set of normal clusters corresponding to a normal cell lineage.
Figure 20A:
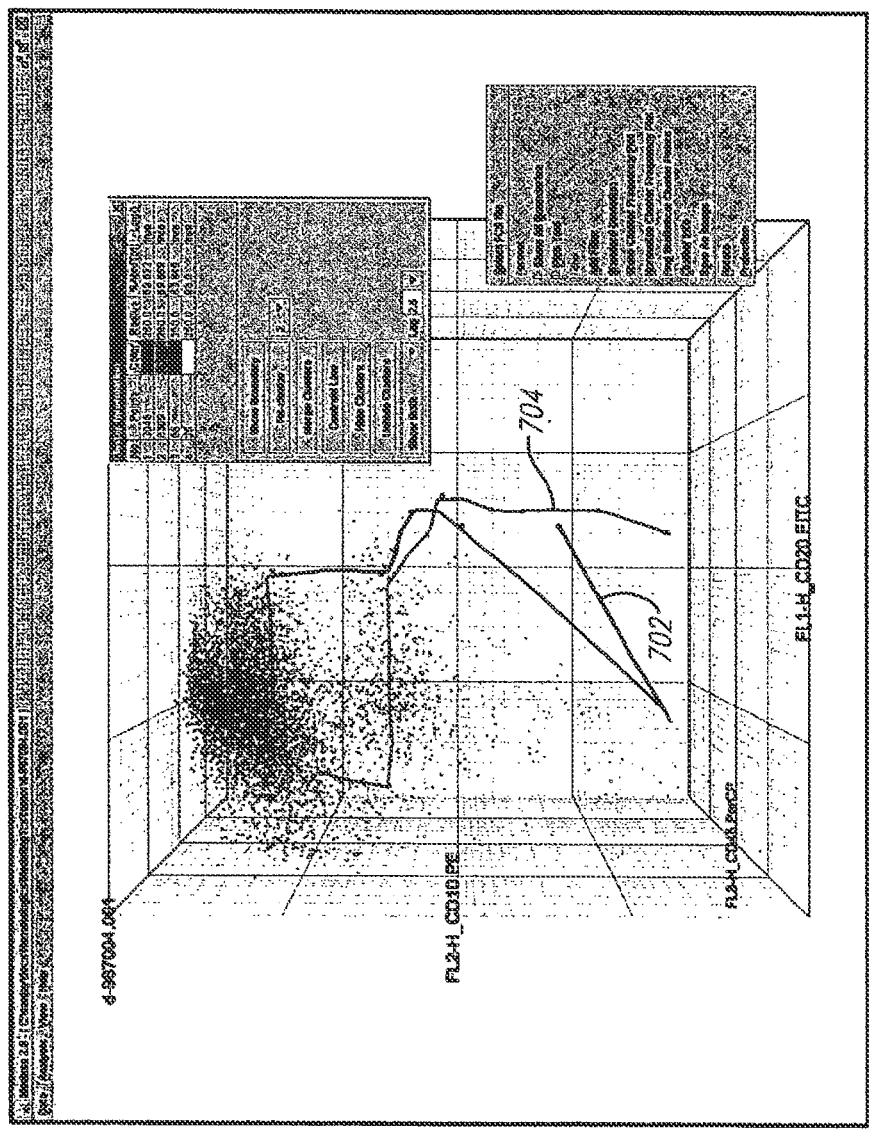
FIGS. 20A and 20B are illustrations of multi-dimensional data projected into pseudo three-dimensional displays generated by a system, such as the system illustrated in FIG. 1.
Figure 20B:
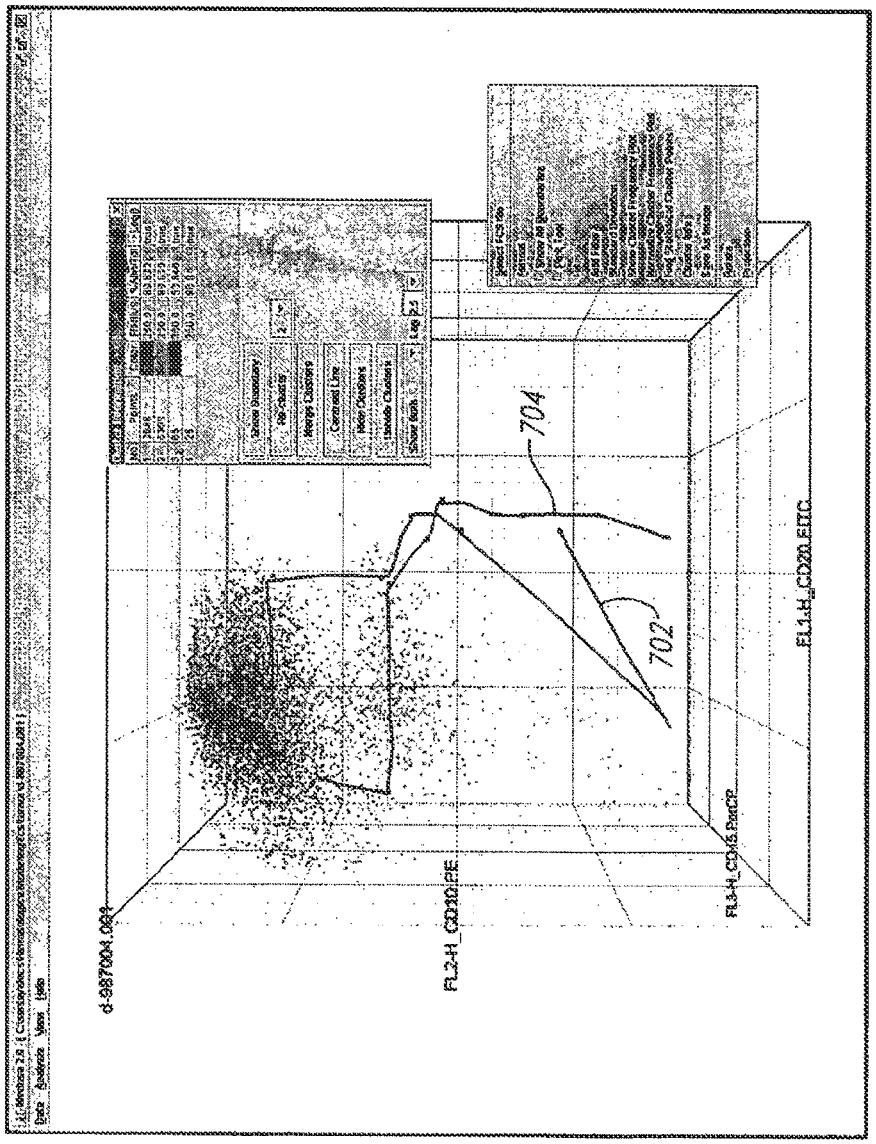

FIG. 19 is a flow diagram for an example subroutine 600 that may be employed by a diagnostic system, such as the diagnostic system 104 illustrated in FIG. 1, to define a normal centroid line for a set of clusters. FIGS. 20A and 20B (collectively FIG. 20) illustrate graphic representations of the data, a reference centroid line 702 and a calculated normal centroid line 704 from the study.

The subroutine 600 starts at 602 and proceeds to 604. At 604, the diagnostic system 104 identifies a set of reference points. For example, the diagnostic system 104 may identify ten reference points selected by a user after viewing various representations of the data set. Alternatively, the diagnostic system 104 may identify a number of statistically selected reference points or may combine input from a user with statistical analysis. In the study, the user selected ten reference points after viewing various representations of the data.

The diagnostic system 104 proceeds to 606, where it defines a reference centroid line based on the identified set of reference points. FIG. 20 illustrates an example reference centroid line 702 defined based on the ten reference points identified by the user in the study.

The diagnostic system 104 proceeds to 608, where it determines the number of clusters in which to group the data. For example, in the study the diagnostic system 104 grouped the data into four clusters based on input from the user. Alternatively, the number of clusters could be determined statistically (by using, for example, dbscan clustering) or by using input from a user in combination with statistical analysis.

The diagnostic system 104 proceeds to 610, where it identifies centroid points for the corresponding number of clusters. This can be done by assigning each point to a cluster based on user input or statistical algorithms or on a combination thereof. See the discussion of clustering algorithms above. The respective parameter values for all the points assigned to a cluster are added together then the result is divided by the number of points in the cluster to obtain the parameter value for the centroid point. For example, if the diagnostic system 104 determined at act 608 to group the data into four clusters, the diagnostic system 104 would identify four centroid points, each point corresponding to a cluster. Table 2, produced below, illustrates an example calculation of a centroid point for a cluster containing 5 data points in a 3 dimensional space.

TABLE 2

Example Calculation of Centroid Points

| | X-parameter | Y-parameter | Z-parameter |
|---|---|---|---|
| Point 1 | 25 | 30 | 400 |
| Point 2 | 30 | 35 | 390 |
| Point 3 | 25 | 35 | 395 |
| Point 4 | 25 | 37 | 390 |
| Point 5 | 20 | 33 | 392 |

The number of points, the number of dimensions and the parameter values for Table 2 were selected for ease of illustration.

The diagnostic system 104 proceeds to 612, where it determines a corresponding nearest point on the reference centroid line for each identified centroid point.

The diagnostic system 104 proceeds to 614 where it calculates the difference between each centroid point and the nearest point on the reference centroid line. In the study this was done using the squared distance formula discussed above, without weighting. See Equation 1.

The diagnostic system proceeds to 616, where it adjusts the reference points based on the centroid points and the nearest reference points. In the study, this was done by adding the difference between the centroid point and the nearest point of a cluster to the reference points in that cluster.

The diagnostic system proceeds to 618, where it redefines the reference centroid line using the adjusted reference points and the centroid points for each cluster. In the study, this was done by connecting centroid lines for each cluster using geometric bending. An example redefined reference centroid line is illustrated in FIG. 20 as line 704. The reference centroid line may be further refined using statistical analysis. For example, statistically insignificant points or points outside a defined radius may be removed from the data set. Calculations made by the diagnostic system 104 while employing the subroutine 600 may be stored for later use. For example, in clustering the data during the study the diagnostic system 104 determined the squared distance between the centroid points and the reference points. This data was stored for use in calculating standard deviation values.

The diagnostic system 104 proceeds to 620 where it returns the redefined centroid line and the value of any desired variables, such as user input. The diagnostic system proceeds to 622, where it stops.

In some embodiments, a system 100 may perform other acts not shown in FIG. 19, may not perform all of the acts shown in FIG. 19, or may perform the acts of FIG. 19 in a different order. For example, the subroutine may be made more iterative. For example, the subroutine 600 may be modified so that the system 100 determines after act 616 whether the number of clusters should be modified, and if so returns to act 608. The subroutine 600 may also call other subroutines to perform various functions.

Figure 21:
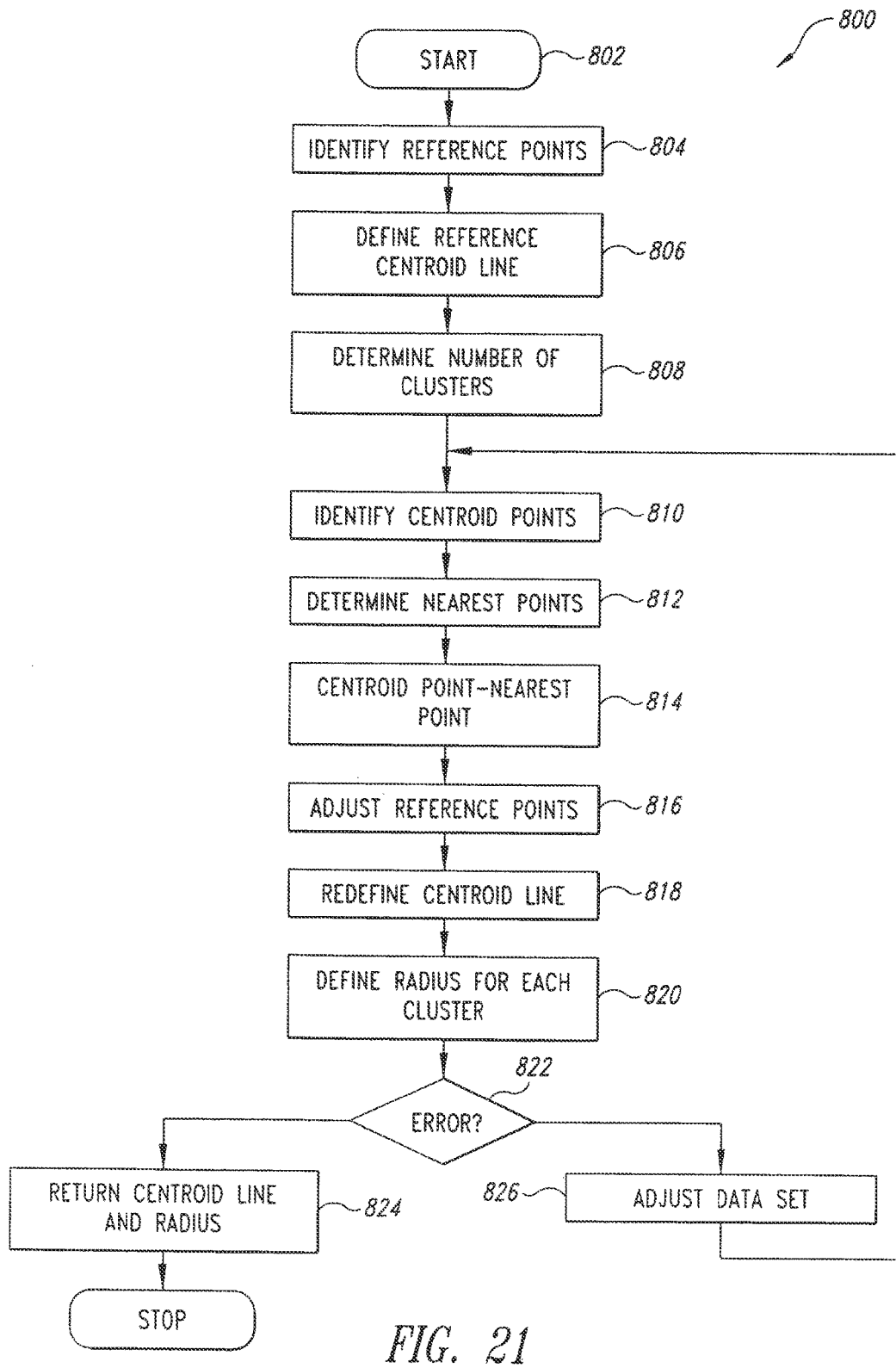
FIG. 21 is a flow chart illustrating operation of a system to define a normal centroid line and radius for a set of normal clusters corresponding to a normal cell lineage.

FIG. 21 is a flow diagram illustrating an example subroutine 800 that may be employed by a diagnostic system, such as the diagnostic system 104 illustrated in FIG. 1, to define a normal centroid line and a normal radius for a set of clusters.

The subroutine 800 starts at 802 and proceeds to 804. At 804, the diagnostic system 104 identifies a set of reference points. For example, the diagnostic system 104 may identify 10 reference points selected by a user after viewing various representations of the data set. Alternatively, the diagnostic system 104 may identify a number of statistically selected reference points or may identify the reference points based on statistical analysis combined with input from a user. In the study, a user selected the reference points after viewing various display representations of the data.

The diagnostic system 104 proceeds to 806, where it defines a reference centroid line based on the identified set of reference points. FIG. 20 illustrates an example reference centroid line 702 defined based on ten points identified by the user in the study.

The diagnostic system 104 proceeds to 808, where it determines the number of clusters in which to group the data. For example, in the study the diagnostic system 104 grouped the data into four clusters based on input from the user.

The diagnostic system 104 proceeds to 810, where it identifies centroid points for the corresponding number of clusters. This can be done by assigning each point to a cluster based on user input or statistical algorithms or, as in the study, on a combination thereof. See the discussion of clustering algorithms above. The respective parameter values for all the points assigned to a cluster are added together then the result is divided by the number of points in the cluster to obtain the parameter value for the centroid point. For example, if the diagnostic system 104 determined at act 808 to group the data into four clusters, the diagnostic system 104 would identify four centroid points, each point corresponding to a cluster.

The diagnostic system 104 proceeds to 812, where it determines a corresponding nearest point on the reference centroid line for each identified centroid point.

The diagnostic system 104 proceeds to 814 where it calculates the difference between each centroid point and the nearest point on the reference centroid line. In the study this was done using the squared distance formula discussed above, without weighting. See Equation 1.

The diagnostic system 104 proceeds to 816, where it adjusts the reference points based on the centroid points and the nearest reference points by using input from the user, statistical analysis or a combination thereof. In the study, the difference between the centroid point and the nearest point of a cluster was added to the reference points in that cluster.

The diagnostic system 104 proceeds to 818, where it redefines the reference centroid line using the adjusted reference points and the centroid points for each cluster. In the study, this was done by connecting centroid lines for each cluster using geometric bending. An example redefined reference centroid line is illustrated in FIG. 20 as line 704.

The diagnostic system 104 proceeds to 820, where it defines a radius for the set of clusters. As noted above, the radius may be a function of position on the reference centroid line or in the n-dimensional space. The reference centroid line and radius may form various cluster shapes. For example, spherical clusters, hyperspheres or hyperellipsiods may be defined by the reference centroid line and radius. Clusters may be shaped like sausages or barbells or various other shapes. In the study, the user entered a radius for each cluster in the normal set of clusters, the radius being a distance from a nearest point on the reference centroid line.

The diagnostic system 104 proceeds to 822, where it determines whether an error criteria is satisfied. For example, the diagnostic system 104 may determine whether a statistically insignificant number of points are outside the clusters defined by the reference centroid line and radius. If the error criteria is satisfied, the diagnostic system 104 proceeds to 824, where the subroutine returns the defined centroid line and radius for the data set, as well as any other desired variables. If the error criteria is not satisfied, the diagnostic system 104 proceeds to 826, where it adjusts the data set. For example, the diagnostic system 104 may determine that statistically insignificant points in the data set should be disregarded. The diagnostic system 104 returns to 810, for further processing of the adjusted data set.

Some embodiments of a system 100 may perform other acts not shown in FIG. 21, may not perform all of the acts shown in FIG. 21, or may perform the acts of FIG. 21 in a different order. For example, the subroutine may be made more iterative. The subroutine 800 may also call other subroutines to perform various functions. For example, the subroutine 800 may call a subroutine to determine whether the identified clusters should be reclustered, such as the subroutine 900 illustrated in FIG. 22.

Figure 22:
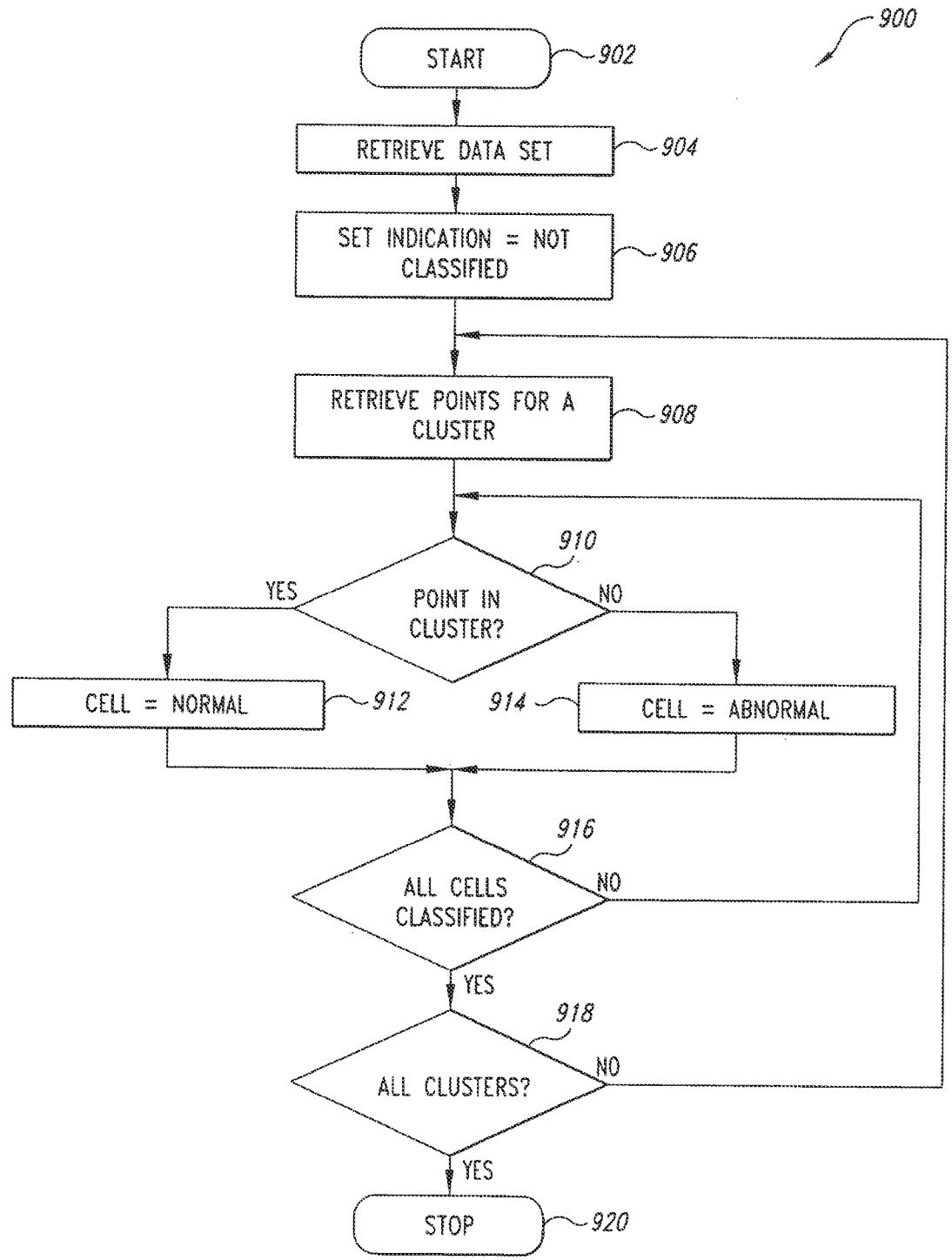
FIG. 22 is a flow chart illustrating operation of a system to determine whether points in a test set of data are contained within a set of normal clusters in an n-dimensional space.

FIG. 22 is a flow diagram illustrating an example subroutine 900 that may be employed by a diagnostic system, such as the diagnostic system 104 illustrated in FIG. 1, to determine whether points in a data set are contained within a set of clusters defined by a centroid line and radius. This information can be used by the diagnostic system 104 to, for example, determine whether a defined set of normal clusters should be redefined because too many cells are classified as abnormal, or to detect abnormal cells in a test set of cells.

The subroutine starts at 902 and proceeds to 904. At 904 the diagnostic system 104 retrieves the data set and proceeds to 906. At 906 the diagnostic system 104 sets a data field associated with each point in the data set to indicate that the subroutine has not yet classified the point and proceeds to 908.

At 908 the diagnostic system 104 retrieves the points associated with a selected cluster from the data set and proceeds to 910. At 910 the diagnostic system 104 determines whether an unclassified point associated with the selected cluster is within the centroid line and radius for the selected cluster. This can be done by, for example, computing the distance between the unclassified point and the nearest point on the centroid line for the cluster, classifying the point as normal if the distance is less than the radius of the cluster at the nearest point on the centroid line, and classifying the point as abnormal if the distance is not less than the radius of the cluster at the nearest point on the centroid line.

If the diagnostic system 104 determines at 910 that the point is within the selected cluster, the diagnostic system 104 proceeds to 912 where it classifies the cell as normal and indicates that the cell has been classified. If the diagnostic system 104 determines at 910 that the point is not within the selected cluster, the diagnostic system 104 proceeds to 914 where it classifies the cell as abnormal and indicates that the cell has been classified. The same data field can be employed to indicate whether a cell is unclassified, is classified as normal, or is classified as abnormal. Alternatively, two or more data fields may be employed to indicate respectively whether a cell has been classified and if so whether the cell is normal or abnormal.

The diagnostic system 104 proceeds from 912 or 914 to 916, where it determines whether all cells associated with the selected cluster have been classified. If the answer at 916 is NO, the diagnostic system 104 returns to 910. If the answer at 916 is YES, the diagnostic system 104 proceeds to 918. At 918 the diagnostic system 104 determines whether all clusters in the set of clusters have been processed. If the answer at 918 is NO, the diagnostic system 104 returns to 908. If the answer at 918 is YES, the diagnostic system 104 proceeds to 920, where the subroutine 900 stops.

Some embodiments of a system 100 may perform other acts not shown in FIG. 22, may not perform all of the acts shown in FIG. 22, or may perform the acts of FIG. 22 in a different order. For example, the subroutine 900 may be modified to process a data set sequentially, instead of processing the data a cluster at a time and without setting an indicator for whether a data point has been classified. The subroutine 900 may also call other subroutines, for example, the subroutine 900 may call a subroutine to calculate the distance between a point and the nearest point on a centroid line.

Data generated by the system 100, including data generated to define a normal cell lineage and data from a test sets of cells, may be represented in various formats and used for various purposes. For example, as discussed above, the data may be displayed as multiple 2 by 2 projections of the multi-dimensional data in a Cartesian coordinate system or as pseudo three-dimensional projections of the multi-dimensional data in a Cartesian coordinate system. See FIGS. 4-10 and 12-17, and 20, discussed above. Color or shading can be used to show additional dimensions. These methods of displaying the data are particularly helpful to the user in defining and redefining a normal centroid and radius for a given maturation lineage.

Figure 23A:
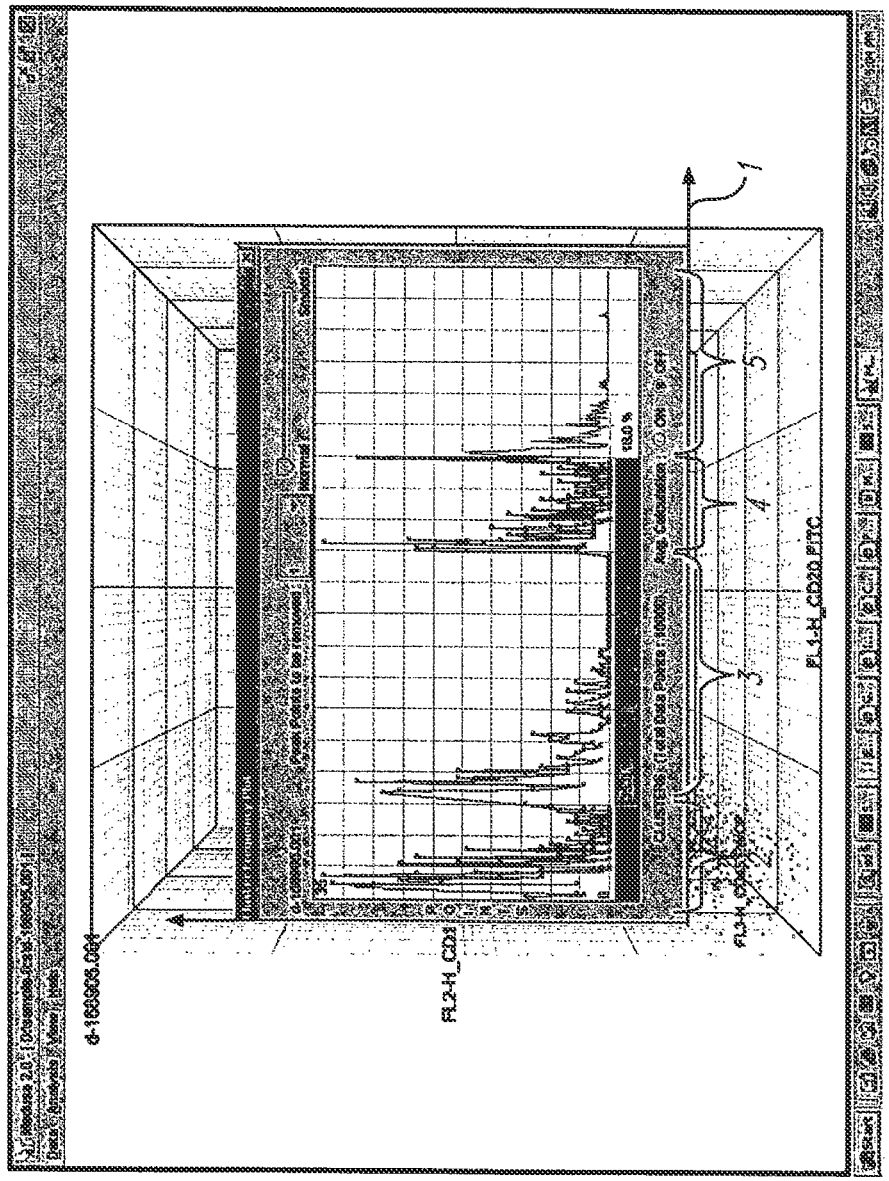
FIGS. 23A and 23B are illustrations of multi-dimensional data projected into pseudo three-dimensional displays generated by a system, such as the system illustrated in FIG. 1.
Figure 23B:
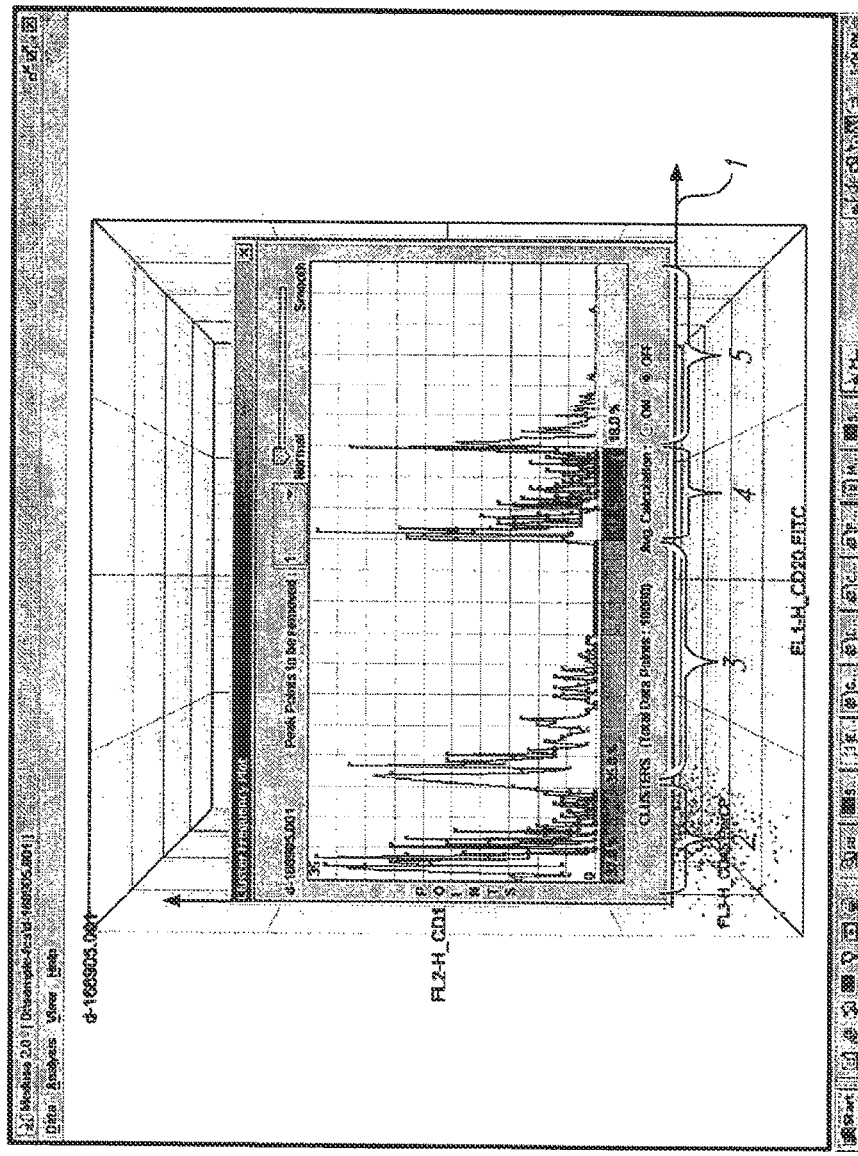

The data can also be displayed as a two-dimensional plot of continuous cell frequency along a defined centroid line. The position along the centroid line corresponds to a measure of time within the maturation process. Thus, a histogram may be generated displaying the group distribution of cells throughout the maturation process. FIGS. 23A and 23B (collectively FIG. 23) illustrate plotting of a sampled continuous cell frequency along a defined normal centroid line for a B lymphoid cell lineage. A horizontal axis 1 corresponds to position along the defined centroid line. Four clusters 2, 3, 4, 5, corresponding to stages of maturation, are identified along the horizontal axis 1. A vertical axis 6 corresponds to the number of points in the data set at various sample points along the centroid line. In FIG. 23, 108 sample points were selected for the centroid line as follows. Ten reference points along the centroid line were identified. Midpoints along the centroid line were calculated for the ten reference points, yielding 19 points. Six midpoints were then calculated for the 19 points, yielding 108 points. The percentage of total data points sampled for each cluster is displayed as well.

Additional specimens may be used to define the normal centroid and radius. For example, the two-tube, 4 color panel process described above could be used to stain a larger number of bone marrow specimens exhibiting normal antigen expression. These specimens could be selected from routine work flow, and may include specimens from bone marrow donors, patients without hematologic neoplasms, and patients post transplant with 100% donor chimerism who were transplanted for diseases that were not ALL. The specimens may include both pediatric and adult specimens. The additional specimens may be random, or selected with respect to desired criteria, such as sex, age or minority group. It is expected that selection by sex, age or minority group will not result in significant differences in the defined normal centroid and radius for B lymphoid maturation lineage.

The expanded data set may be used to assess the variability of cluster positions for the individuals from whom specimens are collected as well as differences in composition that are expected in a routine analysis of specimens. The data set may also include and/or be compared with data from patients with abnormal bone marrow specimens that are not a result of a clonal or neoplastic process, such as specimens from patients early post stem cell transplant containing only the most immature cells or patients treated with Rituxan (anti-CD20). In these patients the B lymphoid development in the bone marrow is truncated at the beginning of Stage II with any cells expressing CD20 being eliminated by the drug. The data set may also be compared to peripheral blood specimens that will contain only Stage IV cells.

Figure 24:
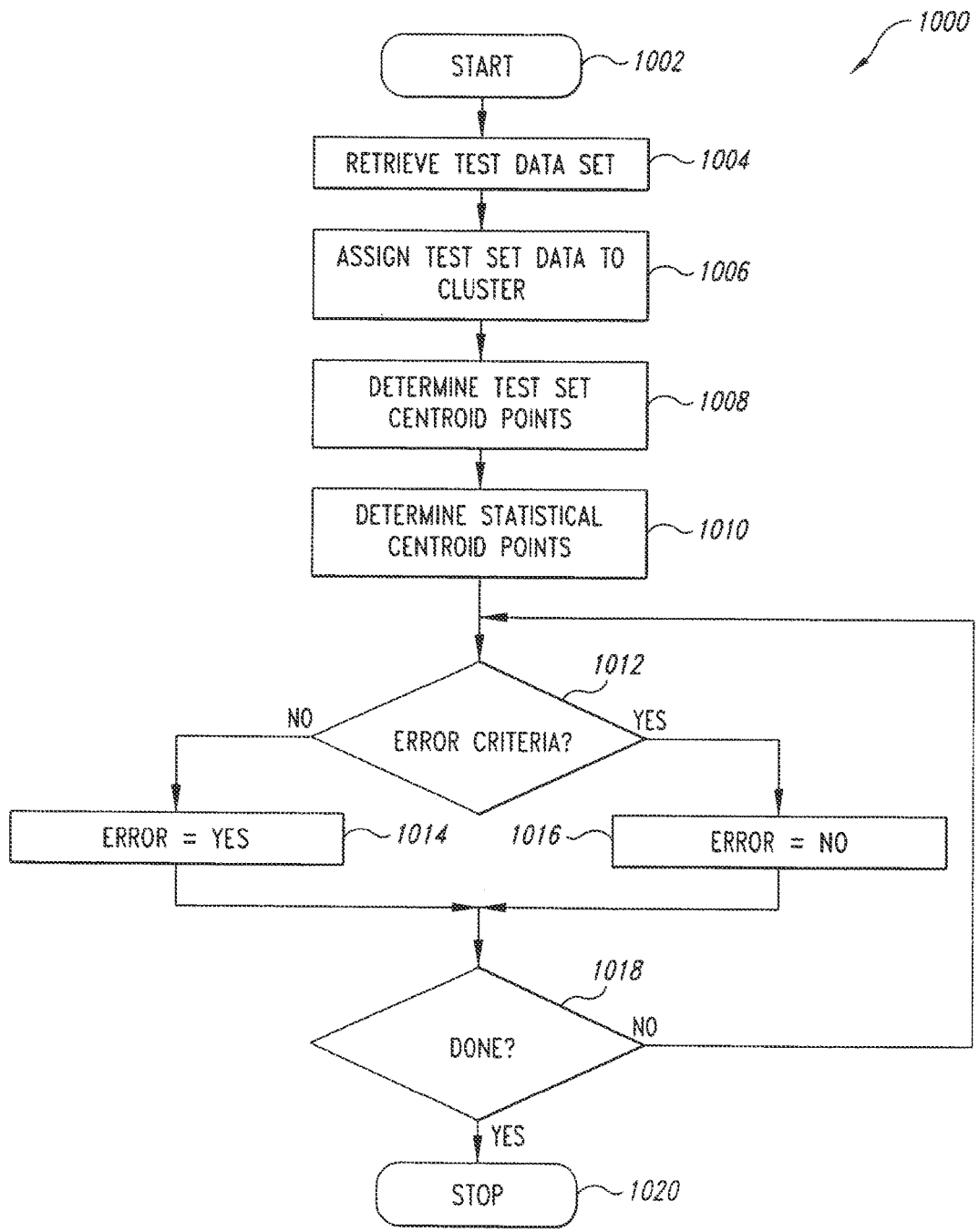
FIG. 24 is a flow chart illustrating operation of a system to compare a test set of data to defined centroid points for a set of normal clusters.

FIG. 24 is a flow diagram for an example subroutine 1000 that may be employed by a diagnostic system, such as the diagnostic system 104 illustrated in FIG. 1, to compare a test set of data to a normal set of clusters defined by centroid points. This information can be used by the diagnostic system to, for example, determine whether a defined normal set of clusters should be redefined.

The subroutine starts at 1002 and proceeds to 1004. At 1004 the diagnostic system 104 retrieves the test data set and proceeds to 1006. At 1006 the diagnostic system 104 assigns the points in the test set of data to clusters, as discussed above, and proceeds to 1008. At 1008, the diagnostic system 104 determines a centroid point for each cluster in the test data set, as discussed above. For example, the diagnostic system could determine the parameter values for the centroid point of a cluster by adding the corresponding parameter values for each point in the cluster and dividing the result by the number of points in the cluster. Alternatively, the diagnostic system could use a statistically adjusted centroid point for the test data set. The diagnostic system 104 proceeds from 1008 to 1010.

At 1010, the diagnostic system 104 determines the corresponding statistical centroid points for each cluster based on previously analyzed data sets. For example, parameter values for a statistical centroid point could be determined by adding the corresponding parameter values for defined centroid points for a set of previously analyzed data sets and dividing the result by the number of data sets. The diagnostic system 104 proceeds from 1010 to 1012.

At 1012, the diagnostic system 104 determines whether an error criteria is satisfied for a cluster in the test data set. For example, the diagnostic system 104 may compare the log of the distance between the centroid point of the cluster and the corresponding statistical centroid point to a threshold value, such as 2.5. If the log of the distance is greater than the threshold value, the diagnostic system 104 may determine that the error criteria is not satisfied. Other error criteria may be employed.

If the diagnostic system 104 determines at 1012 that the error criteria for a cluster in the test data set is not satisfied, the diagnostic system 104 proceeds to 1014, where an indication of an error is set for the cluster in the test data set. If the diagnostic system 104 determines at 1012 that the error criteria for a cluster in the test data set is satisfied, the diagnostic system 104 proceeds to 1016, where an indication of no error is set for the cluster in the test data set.

The diagnostic system 104 proceeds from 1014 or 1016 to 1018, where it determines whether all of the clusters in the test data set have been evaluated. If the diagnostic system 104 determines at 1018 that not all of the clusters have been processed, the diagnostic system 104 returns to 1012. If the diagnostic system 104 determines at 1018 that all of the clusters in the test set have been evaluated, the diagnostic system 104 proceeds to 1020, where the subroutine 1000 stops.

Some embodiments of a system 100 may perform other acts not shown in FIG. 24, may not perform all of the acts shown in FIG. 24, or may perform the acts of FIG. 24 in a different order. For example, the subroutine 1000 may be modified to sequentially compare all data sets in a normal set of data sets to determine which data sets should be removed from the normal set of data sets.

Once the cluster boundaries (normal centroid and radius) are defined for a normal maturation lineage, a test sample can be analyzed by subjecting it to the same reagent exposure and measurement protocols used on the data sets used to define the normal maturation lineage. The results for the test data sample can then be compared to the defined normal maturation lineage, allowing the test sample to be characterized and diagnosed. A system, such as the system 100 illustrated in FIG. 1, need only be provided with the definition of the normal cluster boundaries to diagnose a test sample. Alternatively, the system 100 may be provided with the defined normal data set and the defined centroid line and radius, or the system 100 may be provided with the defined normal data set and may determine the definition of the normal cluster boundaries.

Figure 25:
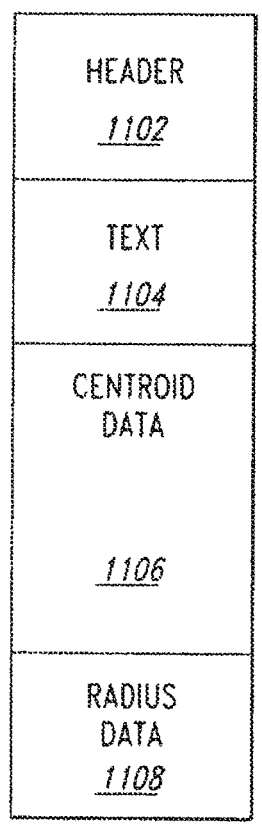
FIG. 25 is a schematic diagram of a data structure suitable for storing information to define a centroid and radius for a set of normal clusters in an n-dimensional space.

FIG. 25 illustrates a data structure 1100 suitable for providing the definitions for the defined normal boundaries for a cell lineage. The data structure 1100 and corresponding instructions can be stored in a computer readable media, such as a memory, which may include the memory 112 illustrated in FIG. 1, or portable memories, such as CD ROMs, floppy disks and/or flash memories, and/or transmitted as a signal in a signal transmission media, such as a wired or wireless media. The data structure 1100 has a header section 1102 describing the locations of the other sections of the data structure 1100. A text section 1104 contains information that describes various aspects of the data structure 1100, such as the number of clusters and how the centroid line and radius are defined. For example, the centroid line may be defined by providing parameters for insertion into an equation or by providing reference points that are to be connected together, or a combination thereof. Similarly, the radius may be defined by providing parameters for insertion into an equation or fixed radius values for a cluster, or a combination thereof. For example, the radius may have a fixed value within one cluster and may be a function of position within a second cluster. A centroid data section 1106 of the data structure 1100 contains information defining the centroid line and a radius data section 1108 contains information defining the radius. If desired, a normal data set used to define the normal centroid line and radius may be provided, either as an additional data field in the data structure 1100 or in a separate data structure, such as the data structure 200 illustrated in FIG. 2.

The individual clusters may also be broken down into subclusters, which can be defined and analyzed using processes similar to those discussed above. For example, the subroutine 800 illustrated in FIG. 21 could be modified to define a centroid line or point and radius for a subcluster and the subroutine 900 illustrated in FIG. 22 could be modified to determine whether a test set of cells contains a subcluster corresponding to a defined subcluster. It is expected that dbscan clustering would be particularly useful in identifying subclusters corresponding to submaturation level within a cluster corresponding to a maturation level within a cell lineage.

A system 100 can be used to diagnose a test data set by comparing the test data set to the defined normal centroid line and radius for the cell lineage. The entire test data set can be compared to the defined normal and displayed by a diagnostic system, such as the diagnostic system 100 in FIG. 1, on a suitable display device or media, such as a raster scan, an active or passive matrix display, or on a passive media, such as paper or vellum. Alternatively, data events in the test data set lying within "normal" positions, specifically B lineage lymphoblasts, may be subtracted from the test data set leaving an "abnormal" data set corresponding to residual populations of potential "abnormal" cells (leukemic lymphoblasts). The remaining abnormal events can then be analyzed and displayed by a diagnostic system, such as the diagnostic system 104 illustrated in FIG. 1, and the user. The remaining abnormal events may define an abnormal subset of the test set of data. Clustering techniques, such as those discussed above, can be used to identify clusters with the abnormal subset of the test set of data and statistical analysis can be employed to determine whether any identified clusters within the abnormal subset are significant.

The system 100 may be tested before being employed to diagnose cancers. For example, a number of specimens from patients with overt ALL may be stained and data collected for comparison to the normal specimens. It is expected that these specimens will have identifiable normal cells that the system 100 will identify as well as CD19 positive leukemic cells that will not fall within the boundaries defined by the normal centroid line and radius. It should be noted that B lineage ALL leukemic cells all express CD19 and, therefore, will be included within the original gating strategy.

Testing of the system 100 may include mixing different proportions of data from the ALL patients with normal specimens to mimic residual disease detection. For example, the system 100 may process 25 normal specimens and generate a defined centroid line and radius for a normal maturation lineage, which the system 100 may store in the memory 112 as digital objects. This information may be looped back with the statistical algorithms on a data file containing an aberrant cell cluster. The cell events confined to the region of normal clusters can be removed with the remaining events representing an "abnormal" cluster. The number and location of tumor cells expected in the mix can be compared to those identified. This can be done both before and after the "normal" cells are subtracted from the test data set.

Smoothing algorithms, including averaging and filtering algorithms, may be employed to smooth the representation of the data. For example, a portion of one cluster could be averaged. For example, it may be known that the average maturation level for a portion of a particular cluster is a significant indicator of whether a test sample is normal, but that individual variances over that portion of the cluster are not significant.

Data for two sets of data may be simultaneously displayed in this manner. For example, data from a test sample may be superimposed over data used to define the normal centroid line. A first color or other indicator could be used to illustrate the normal distribution and a second color or other indicator could be used to illustrate the distribution of the test specimen.

More simplified displays of the data may be employed and compared for visual impact and ease of interpreting normal and/or abnormal development. For example, the proportions of cells in each of the four B lymphoid cell lineage stages may be plotted to represent the clusters identifiable in the data space. The total events in each of the four clusters may be displayed to represent the maturation of cells within normal bone marrow and/or to a test sample against a normal representation. The parameters of abnormal cells that can be depicted include: number of abnormal events, distance from normal, dispersion within the abnormal population, and cellular markers that distinguish the aberrant cells from normal.

Figure 26:
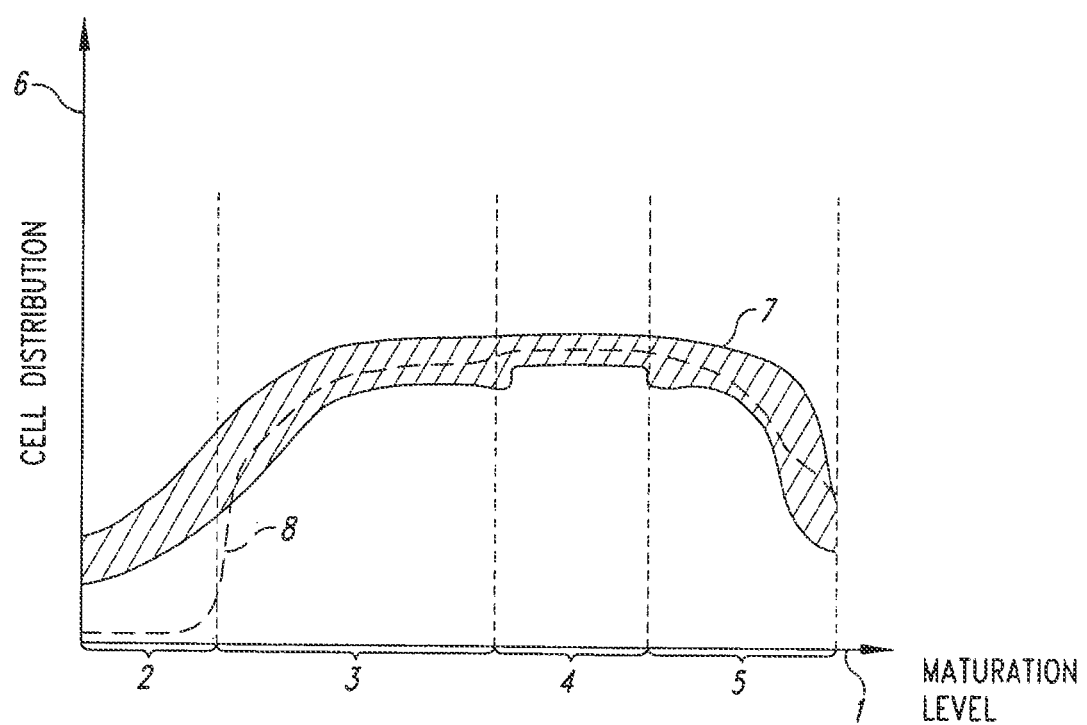
FIG. 26 is an illustration of multi-dimensional data projected into a pseudo two-dimensional display generated by a system, such as the system illustrated in FIG. 1.

FIG. 26 illustrates an example simplified representation of data gathered from a test sample superimposed on a representation of a defined normal data set. A horizontal axis 1 corresponds to an indication of maturation level of a cell lineage and indicates four stages 2, 3, 4, 5, corresponding to maturation level clusters within the cell lineage. A vertical axis 6 corresponds to an indication of the number of cells at various maturation levels. The indication may be, for example a percentage of the total number of cells within a stage or a logarithmic indicator. A band 7 illustrates a defined normal range for a sample. The band 7 may correspond, for example, to a standard deviation for a normal set of cells, or it may correspond to a defined centroid line and radius for a normal set of cells. A dashed-line 8 illustrates the results for a test sample.

A quality control process may be employed. For example, bead preparations may be used to assess instrument performance, such as Rainbow beads (RCP and RFP, Spherotech, Libertyville, Ill.) which are plastic microspheres with dye embedded inside the particle insuring fluorescence stability. The RFP beads have only a single peak in each of the four fluorescence channels and are used as a primary standard. The RCP beads, a mixture of six intensity beads observed in all channels, serve as a secondary standard and provide data regarding linearity for each of the fluorescence detectors. Fluorescence emission spectral compensation is established and monitored by staining normal blood with anti-CD4 antibody conjugated with each of the chromophores used (FITC, PE, PerCP, and APC). Cells stained with these antibodies separately are analyzed to ensure fluorescence from the expected chromophore is detected only in the appropriate fluorescence channel (24). Each lot of reagent used in the assessment of cells is titered before it is placed into inventory. A titer of antibody yielding maximum fluorescence intensity is selected and specificity of reagent is checked for each new lot of antibodies.

Using these quality control procedures, two flow cytometers experimentally generated identical results for the same specimen. In a study of normal adult blood using these quality control procedures, the intensity of CD4 on lymphocytes was found to be almost invariant for 21 individuals assayed on the two instruments collected over a period of eight months. The mean fluorescence intensity of CD4 for these 21 individuals was 1596+/−116 standard deviation fluorescence units resulting in a CV of 7%. These results demonstrate that in a data space with a dynamic range of four decades, the biological variation from individual to individual for this one antigen is essentially nil. The amount of CD4 expressed on lymphocytes is, by itself, a biological standard. The quantification of the centroid line position (measured on immature bone marrow cells) may be compared to the variability of antigens expressed on normal mature blood cells, which will provide a basis for understanding the biological variation between individuals with respect to the intensity of antigen expression during maturation of blood cells not just on mature cells.

The tolerance of a system, such as the system 100 illustrated in FIG. 1, may be determined by changing the target value for the primary standard fluorescent quality control beads by a known amount (factors of 2, and 4). In other words, a system may be detuned by known amounts. Each channel may be tested separately and the channels may be tested together, after establishing proper compensation. For example, Bone marrow cells stained with the four color combinations may be collected under each setting and the data analyzed using the system to be tested. This will assess how far from optimum standard setup a system can operate and still permit correct identification of cells of the stages of development by the system. This performance then defines the tolerance required of a quality control program based on the ability of the system to identify the appropriate cell populations.

As would be recognized by the skilled artisan, the above methods can be used in a number of settings, including but not limited to diagnostics and disease and treatment monitoring.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. The above examples are offered by way of illustration and not by way of limitation. Accordingly, the invention is not limited except as by the appended claims.

What is claimed is:
1. A method, comprising:
   (a) staining cells in a normal set of biological cells using a first protocol, wherein the first protocol includes exposing each cell to four or more detectable reagents which are specific for one or more markers selected from: CD10, CD19, CD20, CD22, CD34, CD38, and CD45;
   (b) measuring a plurality of detected fluorescence intensities that correspond respectively to the four or more detectable reagents as measured by flow cytometry of each cell in the normal set of biological cells using a second protocol;
   (c) mapping each cell in the normal set of biological cells to a corresponding point in an n-dimensional space based at least in part on the measured plurality of fluorescence intensities of the cell in the normal set of biological cells, wherein the corresponding points form a normal set of points;
   (d) defining a set of normal clusters in the n-dimensional space by defining a centroid line and radius based on the mapping of the normal set of points in the n-dimensional space, wherein distance along the centroid line corresponds to maturation level within a cell lineage and the radius is a function of distance along the centroid line;
   (e) staining cells in a test set of biological cells using the first protocol;
   (f) measuring a plurality of detectable fluorescence intensities that correspond respectively to the four or more detectable reagents as measured by flow cytometry of each cell in the test set of biological cells using the second protocol;
   (g) mapping each cell in the test set of biological cells to a corresponding point in the n-dimensional space based at least in part on the measured plurality of fluorescence intensities of the cell in the test set of biological cells, wherein the corresponding points form a test set of points;
   (h) comparing the test set of points to the defined set of normal clusters;
   (i) identifying test points in the test set of points corresponding to cells outside of normal in the test set of cells based on the comparing of the test set of points to the defined set of normal clusters;
   (j) determining a cell concentration of the identified points of (i) at a maturation level; and
   (k) detecting leukemic cells based on the determined cell concentration of (j).

2. The method of claim 1, comprising:
   identifying points in the test set of points which are outside of the set of normal clusters defined by the centroid line and radius.

3. The method of claim 1, comprising:
   clustering the identified points of (i) in the test set of points.

4. The method of claim 1 wherein determining a cell concentration of the identified points at a maturation level comprises determining a cell concentration along the centroid line of (d) defining the set of normal clusters.

5. The method of claim 1 wherein comparing the test set of points to the defined set of normal clusters comprises:
   comparing cell concentrations along the centroid line in the set of normal clusters to cell concentrations along the centroid line in the test set of cells.

6. The method of claim 1 wherein the comparing the test set of points to the defined set of normal clusters comprises representing an indication of a distribution of biological cells of the test set of biological cells along the centroid line in the n-dimensional space in a two-dimensional display having a first axis corresponding to a cell maturation level within a cell lineage and a second axis corresponding to a frequency of occurrence.

7. The method of claim 6, comprising identifying a subset of cells of the test set of biological cells by excluding cells of the test set of biological cells from the subset of cells based on the defined set of normal clusters.

8. The method of claim 1 wherein the first protocol includes exposing each cell to one or more detectable reagents which are specific for one or more markers selected from CD3, CD4, CD8, CD14, CD15, CD16, CD33, and CD56.

* * * * *